(12) United States Patent
Floyd et al.

(10) Patent No.: US 7,286,956 B2
(45) Date of Patent: Oct. 23, 2007

(54) METHODS OF ESTIMATING THE DIMENSIONAL STABILITY OF A WOOD PRODUCT FROM SIMPLE ALGEBRAIC FUNCTIONS OF MOISTURE, SHRINKAGE RATES AND GRAIN ANGLES

(75) Inventors: Stanley L. Floyd, Enumclaw, WA (US); Chih-Lin Huang, Bellevue, WA (US); Mark A. Stanish, Seattle, WA (US)

(73) Assignee: Weyerhaeuser Company, Federal Way, WA (US)

( * ) Notice: Subject to any disclaimer, the term of this patent is extended or adjusted under 35 U.S.C. 154(b) by 20 days.

(21) Appl. No.: 11/313,334

(22) Filed: Dec. 21, 2005

(65) Prior Publication Data

US 2007/0143075 A1  Jun. 21, 2007

(51) Int. Cl.
  *G01B 11/02* (2006.01)
  *G06F 15/00* (2006.01)
(52) U.S. Cl. .................................. 702/159; 702/183
(58) Field of Classification Search .................. 702/33, 702/34, 159, 42, 167, 183; 73/597, 601, 73/602; 428/151, 152, 161; 250/339.06, 250/341.1, 341.8
See application file for complete search history.

(56) References Cited

U.S. PATENT DOCUMENTS

| | | | |
|---|---|---|---|
| 4,606,645 A | * | 8/1986 | Matthews et al. ........... 356/446 |
| 5,992,047 A | * | 11/1999 | Fuller ........................... 34/495 |
| 6,293,152 B1 | | 9/2001 | Stanish et al. |
| 6,305,224 B1 | | 10/2001 | Stanish et al. |
| 6,308,571 B1 | | 10/2001 | Stanish et al. |
| 6,598,477 B2 | | 7/2003 | Floyd |
| 2005/0217382 A1 | | 10/2005 | Floyd et al. |

FOREIGN PATENT DOCUMENTS

| | | |
|---|---|---|
| EP | 0 568 460 B1 | 9/1995 |
| WO | WO 95/31710 A1 | 11/1995 |
| WO | WO 04/045816 A3 | 6/2004 |

OTHER PUBLICATIONS

Nystrom J "Image based methods for nondestructive detection of compression wood in sawn timber," Licentiate Thesis 1999:34. *Lulea Univ Libr 1999*, 1 page.

Nystrom J "Automatic measurement of compression wood and spiral grain for the prediction of distortion in sawn wood products," Doctoral Thesis 2002:37. *Lulea Univ Libr 1999*, 1 page.

(Continued)

*Primary Examiner*—Bryan Bui

(57) ABSTRACT

Methods are provided for estimating the dimensional stability of a wood product from simple algebraic functions of moisture, shrinkage rates and grain angles observed on outer surfaces. The methods may employ single or multiple sensor group measurements. The quantitative relationship between crook or bow stability and lengthwise shrinkage can be established using mathematical operations, rather than sophisticated and complicated finite-element modeling methods. In particular, the curvature of any board length-segment or section, expressed as the second derivative of the crook or bow profile, can be determined from a linear combination of the shrinkage values of the coupons including that segment or section. The overall crook or bow profile of the board can be determined from a section-by-section double-integration of those second derivative values.

12 Claims, 21 Drawing Sheets

OTHER PUBLICATIONS

Thygesen LG, "Determination of dry matter content and basic density of Norway spruce by near infrared reflectance and transmittance spectroscopy," *J Near Infrared Spectr* 2 pp. 127-135 (1994).

Thygesen LG, "NIR measurement of moisture content in wood under unstable temperature conditions—Part 1: Thermal effects in near infrared spectra of wood," *J Near Infrared Spectr* 8 pp. 183-189 (2000).

Thygesen LG, "NIR measurement of moisture content in wood under unstable temperature conditions—Part 2: Handling temperature fluctuations," *J Near Infrared Spectr* 8 pp. 191-199 (2000).

Yeh TF, "Rapid prediction of solid wood lignin content using transmittance near-infrared spectroscopy," *J Agric Food Chem* 52 pp. 1435-1439 (2004).

* cited by examiner

FIGURE 1-PRIOR ART

Moisture Content Profiles at Different Depths in Kiln-Dried 2x10 Lumber
(measured using an electrical-resistance pin-type moisture meter)

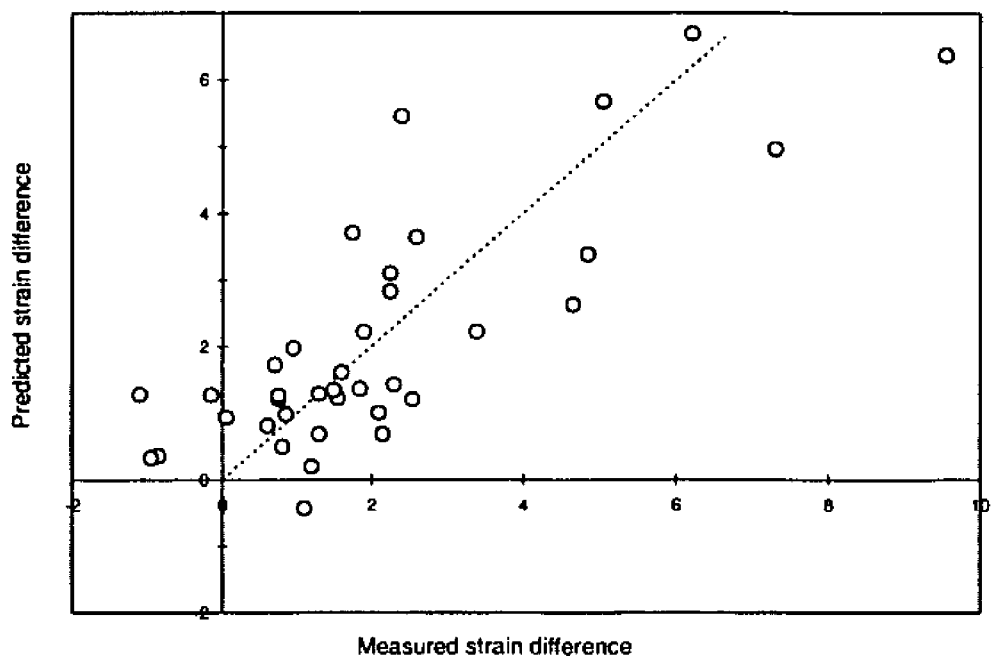
FIGURE 21: 20%RH coupons
Strain difference = 0.02124 * LSR difference + 0.01396 * Inner LSR -
$r^2 = 0.64$

METHODS OF ESTIMATING THE DIMENSIONAL STABILITY OF A WOOD PRODUCT FROM SIMPLE ALGEBRAIC FUNCTIONS OF MOISTURE, SHRINKAGE RATES AND GRAIN ANGLES

FIELD OF THE INVENTION

The present invention generally relates to the use of single and multiple sensor group systems to infer qualitative and/or quantitative estimates of various properties of wood products, including dimensional stability.

BACKGROUND OF THE INVENTION

Wood products, such as logs, boards, other lumber products, or the like, can be graded or classified into qualitative groups by the amount of warp potential, or dimensional stability, in the product. Crook, bow, twist, and cup are examples of warp and are illustrated in FIG. 1. The groups are used to qualitatively represent the warp state at a specified ambient condition or the degree of warp instability of a wood product. The qualitative groups are typically ordinal in nature, though nominal categories may also be used.

Examples of qualitative estimates of warp might be, but are not limited to, low crook, high crook, crook less than 0.5 inches but greater than 0.25 inches, medium bow, bow greater than 1 inch, or like estimates. It might be desirable to classify the warp distortion that a wood product will undergo after it is remanufactured, its moisture redistributes, or it is placed in a new relative humidity environment. Examples of these classifications might be, but are not limited to, low crook at 20% RH, medium crook at 65% RH, high bow at 90% RH, crook greater than 0.5 inches at 20% RH. Wood products can also be characterized in a quantitative manner, such as, an amount of change a wood product will undergo (i.e., crook equal to 0.25 inches). Several known methods for determining quantitative estimates are described below.

The degree of warp depends on several known factors, such as density, modulus of elasticity (hereinafter referred to as "MOE"), moisture content variation, pith location, compression wood, grain angle and others. Many of these factors can be quantitatively or qualitatively evaluated with different types of sensors. For example, MOE can be estimated from the propagation of sound through wood, and specific gravity can be estimated from the capacitance of wood. A different type of sensor group or system may be utilized for detecting each of these properties.

During the three year period from 1995 to 1998, solid sawn softwood lumber usage in wall framing, floor framing and roof framing dropped by 9.9%, 17.2% and 11% respectively in the United States (Eastin et al., 2001)[1]. In this survey of nearly 300 builders, lumber straightness was rated the most important factor affecting buying decisions; yet of all the quality attributes surveyed, dissatisfaction with straightness was highest. It is generally recognized that softwood lumber will continue to lose market share unless the industry improves the in-service warp stability of its product.

[1]Eastin, I. L., Shook, S. R., Fleishman, S. J., Material substitution in the U.S. residential construction industry, 1994 versus 1988, Forest Products Journal, Vol. 51, No. 9, 31-37.

Some wood product applications are intolerant of significant dimensional change (thickness, width, length) after the product is put in service. For example, instability of thickness or width dimensions can cause interference problems for tight-tolerance applications, such as doors and windows. Length instability of wood used in truss chords can result in a problem known as truss uplift; where the truss can raise above interior wall plates forming a gap between the ceiling and interior wall.

In the United States, most softwood dimension lumber is visually graded for a variety of attributes that affect its appearance and structural properties. These attributes include knots, wane, dimension (thickness, width, and length), decay, splits and checks, slope-of-grain, and straightness (warp). Strict quality control practices overseen by third party grading agencies are in place to ensure that all lumber is "on-grade" at the point the grade is assigned. Unfortunately, the straightness and dimension of a piece are not static and can change after the piece is graded. Additional warp and size change can develop after the piece is in the distribution channel or after it is put into service. Typical moisture content of fresh kiln dried lumber averages 15% but ranges from 6% to 19%. This lumber will eventually equilibrated to a moisture ranging from 3% to 19% depending on time of year, geography and whether the application is interior or exterior (Wood Handbook)[2]. This moisture change results in changes in both dimension and warp properties. Any piece of lumber is prone to develop additional "in-service" warp if a) its shrinkage properties are not uniform and it changes moisture or b) its moisture content is not uniform at the point the original grade was assigned. Neither of these conditions is detectable with traditional visual grading methods. Customers of wood products seek stability in both dimension and warp properties.

[2]Wood Handbook, General Technical Report 113 (1999) Department of Agriculture, Forest Service, Forest Products Laboratory.

The wood handbook[2] provides guidelines for assessing the width and thickness stability of solid sawn lumber. Average thickness and width shrinkage is governed by grain orientation as well as radial and tangential shrinkage properties. These average radial and tangential shrinkage values vary by species and are reduced if heartwood is present. Although these methods can be used to estimate the average thickness and width shrinkage behavior of a species, methods for precise quantification do not exist. There are even fewer design tools for estimating length shrinkage.

A number of studies (e.g. Johansson, 2002[3] and Beard et al., 1993[4]) have attempted to define visual indicators that correlate with warp stability. Candidate indicators have included features such as percent juvenilewood, grain orientation, compressionwood, pith location, wane, knot properties and growth rate. Although these studies demonstrate that spiral grain can be a useful predictor of twist stability, they generally agree that there are no reliable visual indicators of crook and bow stability.

[3]Johansson, M., and Kliger, R., Influence of material characteristics on warp in Norway Spruce studs, Wood and Fiber Science, 34(2). 2002, pp 325-336, 2002 by the Society of Wood Science and Technology
[4]Beard, J. S., Wagner, F. G., Taylor, F. W., Seale, R. D., The influence of growth characteristics on warp in two structural grades of southern pine lumber, Forest Products Journal, Vol. 43, No. 6, pp 51-56.

Several theoretical models have also been developed to help explain how moisture and various wood properties interact to cause distortion. Nearly fifty years ago, a mathematical model was developed to explain lumber twist as a function of spiral grain angle, distance from pith, and rate of tangential shrinkage during moisture loss (Stevens et al., 1960[5]). Other recent work has sought to develop finite element models to predict crook and bow distortion (Ormarsson et al., 1998[6]) as a function of three-dimensional patterns of density, growth rings, moisture, modulus of elasticity, etc. Another finite element model is described in a series of U.S. Pat. (Nos. 6,308,571; 6,305,224; and 6,293, 152) to Stanish et al. All of these models teach that the fundamental cause of lumber warp is related to the fact that it shrinks significantly when it dries and this shrinkage is both anisotropic and highly non-uniform. Prediction of warp stability of a wood product is made even more difficult by the fact that its moisture content changes with the vapour pressure of the surrounding environment and this "equilibrium moisture" can be highly variable between two locations within a piece depending on the chemistry and fibre differences between those two locations.

[5]Stevens, W. C., and Johnston, D. D., Distortion caused by spiralled grain, Timber Technology, Jun. 1960, pp 217-218.

[6]Ormarsson, S., Dahlblom, O., Petersson, H., A numerical study of the shape stability of sawn timber subjected to moisture variation, Wood Science and Technology 32 (1988) 325-334, Springer-Verlag 1998.

Today the patterns of equilibrium moisture and shrinkage coefficients within a full size lumber product can be accurately measured only in a laboratory environment. The laboratory technique involves cutting the piece of lumber into small "coupons" and measuring the moisture content and shrinkage coefficients using ASTM standards D-4492 and D-143, respectively. Although much is known about equilibrium moisture and shrinkage behavior of wood, there are as yet no comprehensive theoretical models and no methods of monitoring these properties in a real time production environment.

Much of the fundamental research to develop shrinkage models for wood was done several decades ago. Shrinkage is known to be related to microfibril angle (Meylan, 1968[7]). This relationship is best where microfibril angle is in the range of 30° to 40° and outside this range, the relationship is rather poor. Wooten (Wooten, 1967[8]) observed that longitudinal shrinkage of high microfibril angle wood (>40 degrees) in seedlings seemed to correlate with the thickness of the $S_1$ layer—although no data was presented. Cave (Cave, 1972[9]) proposed a shrinkage theory which includes effects of the $S_1$ layer. More recently, Floyd (Floyd, 2005[10]) demonstrated that certain hemicellulose components, particularly galactan, interact with microfibrils to affect longitudinal shrinkage rates. This combined work suggests that measurements relating to microfibril angle and wood hemicellulose chemistry should be useful in predicting shrinkage patterns in wood.

[7]Meylan, B. A., Cause of high longitudinal shrinkage in wood, Forest Products Journal, Vol. 18, No. 4, Apr. 1968, pp 75-78.

[8]Wooten, T. E., Barefoot, A. C., and Nicholas, D. D., The longitudinal shrinkage of compression wood, Holzforschung. Bd. 21 (1967), Heft 6, pp 168-171.

[9]Cave, I. D., A theory of the shrinkage of wood. Wood Sci. Tech (1972), 6:284-292.

[10]Floyd, S. "Effect of Hemicellulose on Longitudinal Shrinkage in Wood." In The Hemicelluloses Workshop 2005: WQI Limited—New Knowledge in Wood Quality. Conference held in The Wood Technology Research Centre. University of Canterbury New Zealand. 10-12 Jan. 2005, edited by Kenneth M. Entwistle and John C. F. Walker, 115-. Christchurch, New Zealand, 2005.

Several researchers have recently reported some success using these approaches to estimate shrinkage properties. The above referenced patents issued to Stanish et al. teach a method of inferring shrinkage behavior by interpreting patterns of acoustic or ultrasound propagation velocity (related to microfibril angle). Several recent patents and publications have begun to disclose methods of estimating shrinkage coefficients which are more compatible with a high speed lumber manufacturing process. For example, Nystom (Nystrom et al.[11]) demonstrated the relationship between longitudinal shrinkage and an optical property of wood ("tracheid-effect") that is also related to microfibril angle. The "tracheid effect" is taught in U.S. Pat. No. 3,976,384 issued to Matthews et al. A large number of recent publications and patents (e.g. Kelley et al.[12]) teach a method of inferring shrinkage properties by using chemometric methods of near infrared spectroscopy (NIRS). NIRS is of particular interest because the method is sensitive to both physical attributes of the fibres (e.g. microfibrils) and chemical attributes (e.g. hemicellulose).

[11]Nystrom, J.; Hagman, O.; Methods for detecting compression wood in green and dry conditions., Proceedings of the SPIE—The International Society for Optical Engineering (1999) vol. 3826, p. 287-94.

[12]Kelley, S.; Rials, T.; Snell, R.; Groom, L.; Sluiter, A; Wood Science and Technology (2004), 38(4), 257-276

Unfortunately, none of the individual methods described above are accurate enough to give adequate estimates of the dimensional stability of a single piece of lumber. Thus, a need exists for the use of single or multiple sensor systems to provide a qualitative and/or quantitative estimate of the current or future warp distortion of the wood product or of warp-related properties of the wood product.

BRIEF DESCRIPTION OF THE DRAWINGS

The embodiments of the present invention are described in detail below with reference to the following drawings:

FIG. 21 is a plot of measured strain difference versus predicted strain difference.

DETAILED DESCRIPTION OF THE INVENTION

Figure 1:
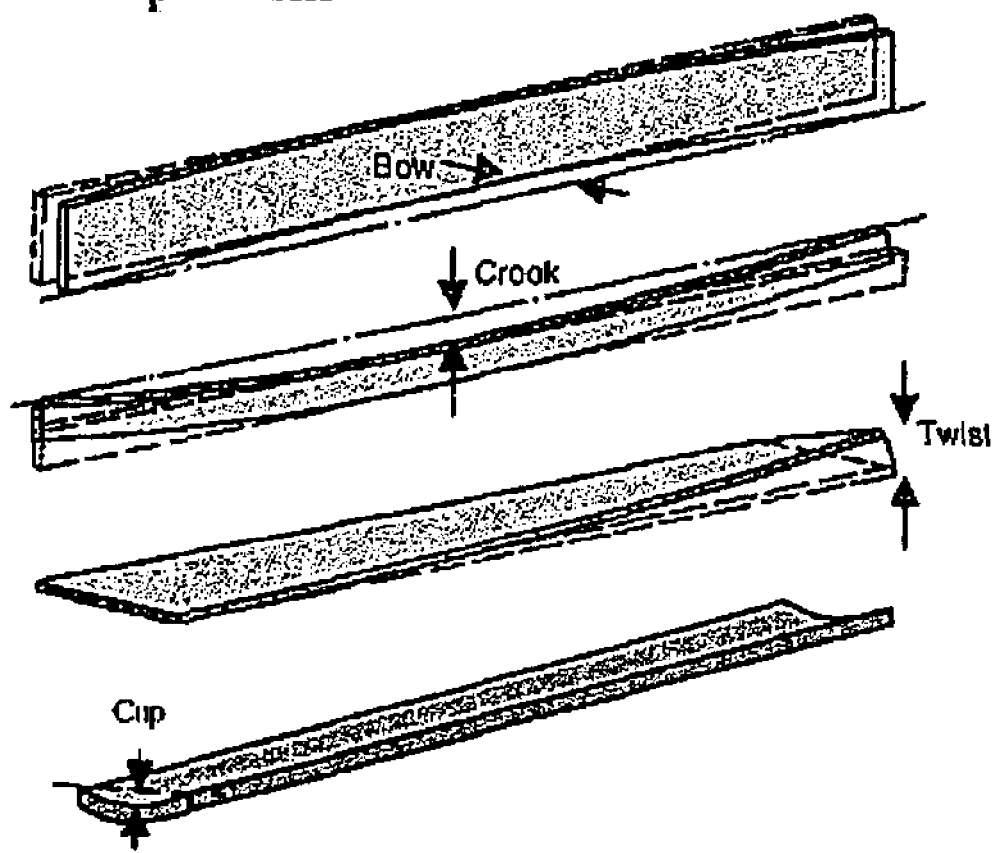
FIG. 1 provides examples of crook, bow, twist, and cup in a wood product.

The present invention generally relates to a variety of methods for obtaining and validating improved estimates of shrinkage patterns, moisture patterns and warp stability for a wood product. The term "wood product" may be interpreted to mean a board, log, other type of lumber, or the like. The methods involve the use of single and/or multiple sensor group systems to provide qualitative and/or quantitative estimates. It has been discovered that estimates of dimensional stability can be much improved when an assortment of measurements are used together, where each measurement contributes information relating to one or more variables. The measurements may be taken at one or more sections of the wood product, which may differ in size given a particular embodiment. The properties observed at the one or more sections may allow a qualitative and/or quantitative estimate of dimensional stability of a region of interest. In a first embodiment, the region of interest may be a coupon or other portion of the wood product. In another embodiment, the region of interest may overlap with one or more sections of the wood product. In another embodiment, the region of interest may be the entire wood product. In yet another embodiment, the region of interest may be the same as the one or more sections detected by the sensor group(s). In another embodiment, the region of interest does not have an overlap with the one or more sections. The dimensional stability assessed may be cup, crook, bow, twist, length stability, thickness stability, width stability, or any combination of these. Provided below are various embodiments of the present invention:

A. Methods of Using Multiple Sensors (Sensor Fusion) to Provide Qualitative and/or Quantitative Assessments via Analysis of Regions of Interest in a Wood Product Where Non-Uniformity of Composition (e.g. Moisture), Shrinkage Rate or Grain Angle May Result in warp Instability of the Wood Product In an embodiment of the present invention, a classification algorithm may be created to classify a wood product into one of a plurality of groups or categories. The groups may be based on qualitative or quantitative characteristics. For example, in an embodiment, the categories may be different grades. Warp classification of wood products, such as boards may require inputs from one or more sensor groups detecting properties of the boards. The sensor groups may be a part of those systems previously mentioned for analyzing a wood product. The technologies for these systems are known by those skilled in the art. For example, the sensor groups may obtain moisture content measurement, electrical property measurement, structural property measurement, acousto-ultrasonic property measurement, light scatter (tracheid-effect) measurement, grain angle measurement, shape measurement, color measurement, spectral measurement and/or defect maps. Structural property measurement may measure modulus of elasticity, density, specific gravity, strength, or a combination of these. Acousto-ultrasonic property measurement measures may measure velocity and/or damping. The spectral measurement may be characterized by absorption or reflectance values over a wavelength spectrum ranging from ultraviolet through near infrared.

Using this approach, the prediction model or algorithm of the present invention may use inputs of many different resolution scales. Some examples are board average MOE, moisture content measured across the width of the board in one foot increments along the length of the board, spectroscopy data collected every inch, or laser data collected every ¼ inch.

The inputs are functions of the sensor signals and may be either quantitative or qualitative. For example, an input could be the estimated moisture content for each 12 inch lineal section of a piece of lumber, as estimated by a moisture meter. Another example is an indicator for the presence or absence of a knot in a 12 inch by 1 inch section of wood, based on a color image. Inputs may be direct sensor measurements, pre-processed signals, combined signals from several sensors or predicted measures from other sensors. Signal pre-processing may include, but is not limited to, such steps as filtering, smoothing, derivative calculations, power spectrum calculations, Fourier transforms, etc., as is well known in the art. Predicted measurements from other sensors may include, but are not limited to, shrinkage-coefficients predicted from sensors which measure the light scattering and light absorption properties of wood and used as inputs to a partial least squares, or "PLS", prediction model.

The prediction algorithm(s) or model(s) based on the set of inputs can be derived using many techniques which include, but are not limited to, regression trees, classification trees, linear discriminant analysis, quadratic discriminant analysis, logistic regression, Partial Least Squares or other supervised learning techniques such as neural networks. There are many forms of equations or algorithms that could be used, and a general reference is Hastie, et al[13].

[13]Hastie, T., Tibshirani, R., and Friedman, J., (2001) The Elements of Statistical Learning, Springer, N.Y.

These algorithms can be developed to classify boards into 2 or more groups. For example, boards might be classified into four grades (#1 grade, #2 grade, #3 grade, #4 grade) or into two classifications (warp and no warp), or into three categories (crook less than 0.25 inches, crook between 0.25 and 0.5 inches, crook greater than 0.5 inches). Typically, the parameters in the models or algorithms are derived from a training-set of data and the performance is tested on a testing-set of data before being used in production, although other approaches exist.

Various embodiments are contemplated involving the use of sensor groups and algorithms. In a first embodiment, a single sensor group may provide inputs to a classification algorithm which classifies wood products into one of a plurality of groups or categories, such as grades, for example.

In a second embodiment, a single sensor group may provide inputs to a classification algorithm as in the previous example. However, in this embodiment, a second algorithm may be selected after classifying the wood product. This second algorithm may be selected from a plurality of algorithms which are used to assess the dimensional stability in a quantitative manner.

In a third embodiment, two or more sensor groups may provide two or more inputs to a classification algorithm to classify wood products into one of a plurality of categories.

In a fourth embodiment, two or more sensor groups may provide two or more inputs to an algorithm for providing a quantitative assessment of dimensional stability of wood products.

In a fifth embodiment, two or more sensor groups may provide two or more inputs to a classification algorithm to classify wood products into one of a plurality of categories. Next, a second algorithm may be selected after classifying the wood product. This second algorithm may be selected from a plurality of algorithms which are used to assess the dimensional stability in a quantitative manner.

The following example illustrates how information from multiple sensors was used to predict a warp classification for lumber.

EXAMPLE 1

Three groups of lumber, each containing approximately 200 8-foot long 2 inch by 4 inch boards, were obtained from a mill. Via the use of multiple sensors, each piece of lumber was measured for crook, bow, average moisture content, ultrasonic velocity and a density profile was obtained. Each piece of wood was then placed in a 20% relative humidity, or "RH" environment for 5 weeks and then measured again for crook and bow. In this example, the objective was to classify the boards into two final warp classes (at 20% RH) using the initial data from multiple sensors. The final warp classes were defined as follows: a board was classified as a "rogue" if the absolute crook at 20% RH was greater than 0.5 inches or the absolute bow at 20% RH was greater than 1.0 inches. Otherwise the board was classified as a "non-rogue".

The initial data from lumber groups 1 and 3 were used to develop and train the classification algorithm and the initial data from boards in group 2 were used to test it. Five inputs were used to develop the classification algorithm: initial absolute crook, initial absolute bow, ultrasonic velocity, initial moisture content and a measure of the variability in board density. The boards from groups 1 and 3 were assigned into the two groups, rogue and non-rogue, based on their final absolute crook and final absolute bow. Using this definition, there were 92 rogues and 309 non-rogues in the training set, groups 1 and 3.

Linear discriminant analysis was used to develop a discriminant function to classify the boards. The table below shows the percentage of boards that were correctly classified as rogue or non-rogue and those that were incorrectly classified in the training set.

TABLE 1

| Put into Group | True Group | |
| --- | --- | --- |
| | Non-Rogue | Rogue |
| Non-Rogue | 280 | 16 |
| Rogue | 29 | 76 |
| Total | 309 | 92 |

Figure 2:
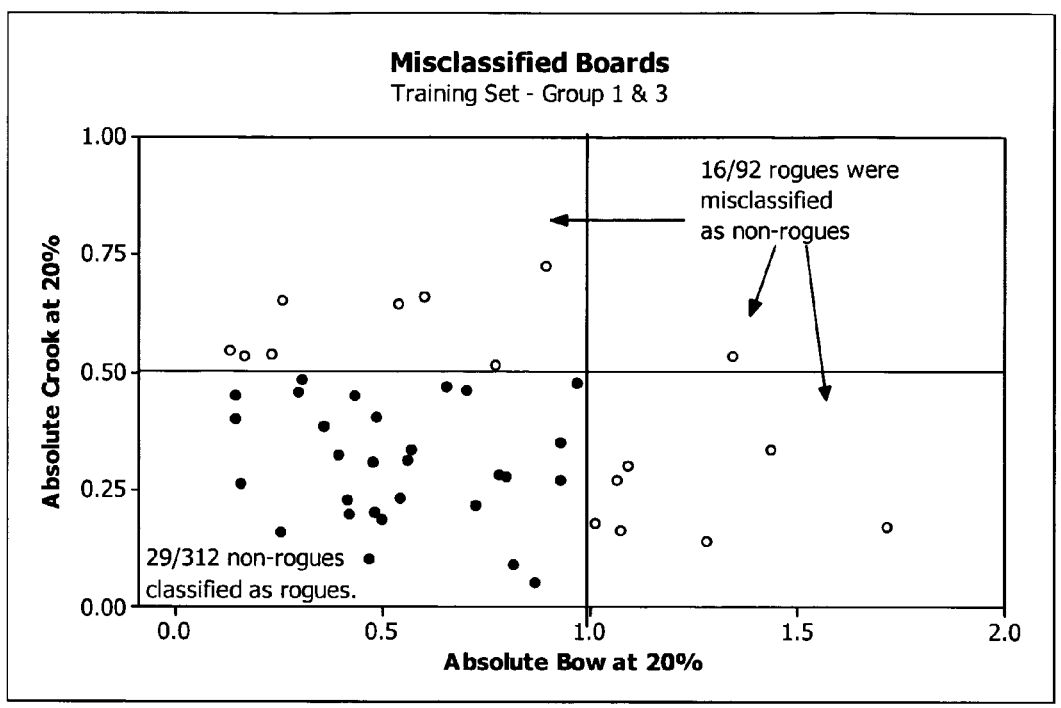
FIG. 2 is a plot of misclassified boards in an embodiment of the present invention.

Eighty-three percent, or 76 out of 92 rogues, were correctly classified as rogues. Ninety-one percent, or 280 out of 309 non-rogues, were correctly classified as non-rogues. FIG. 2 provides a plot of the misclassified boards.

The linear discriminant function developed on the training set was then applied to the test set of boards, group 2. This group had 62 boards assigned as rogues and 143 assigned as non-rogues. The results of the classification using the discriminant function are shown in the table below.

TABLE 2

| Put into Group | True Group | |
| --- | --- | --- |
| | Non-Rogue | Rogue |
| Non-Rogue | 135 | 12 |
| Rogue | 8 | 50 |
| Total | 143 | 62 |

Figure 3:
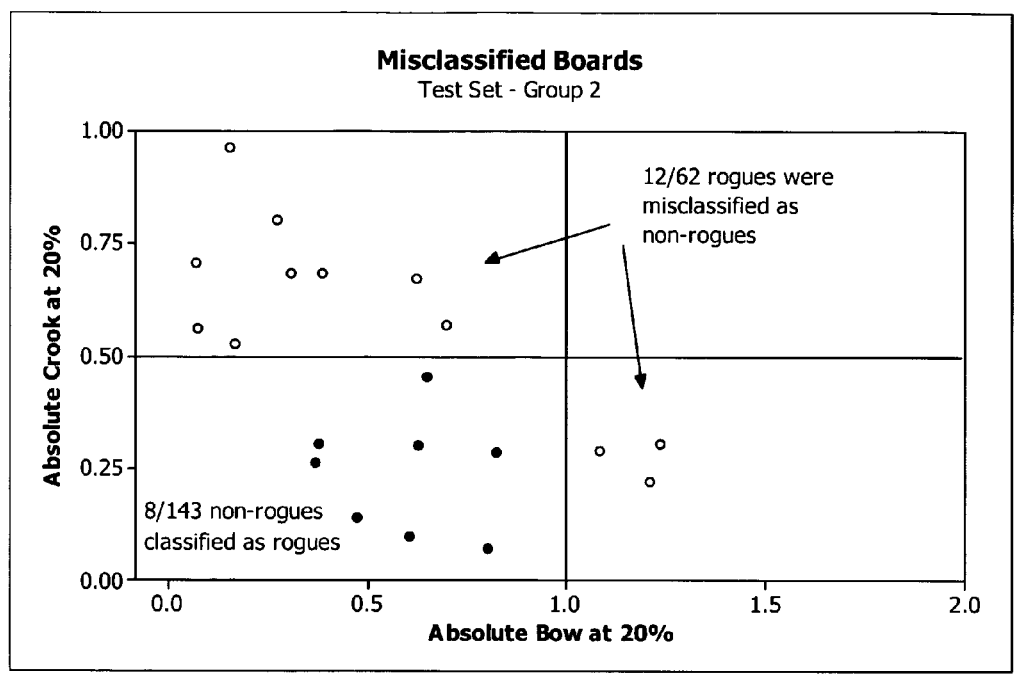
FIG. 3 is a plot of misclassified boards in an embodiment of the present invention.

In this case, 50 of the 62 rogues were correctly classified with the initial data as rogues, which translates to 81% accuracy. Also, 135 non-rogues were correctly classified using the initial data as non-rogues, which translates to 94% accuracy. A graph of the misclassified boards is shown in FIG. 3.

A special case of the methods described above may occur, for example, when the classes that are predicted are existing industry grade classes and an objective is to sort wood products into those grade classes. Another special case occurs when existing grades are not used, but the wood product is to be sorted into new classes developed based on a particular use of the wood product. An example is classifying lumber into categories including those that will warp significantly in dry climates versus those that will not.

Estimates of the cost of misclassification can be used in the creation of the classification models or algorithms. For example, there may be a higher cost associated with a rogue board being classified as a non-rogue, than there is for a non-rogue being classified as a rogue. In these cases, the models and/or algorithms can be developed using these costs in such a way as to minimize the occurrence of the costlier mistake[14].

[14] Ripley, B. D. (1996) *Pattern Recognition and Neutral Networks*, Cambridge: Cambridge University Press.

Shrinkage Rate Coefficient as an Indicator of Dimensional Stability

Wood is a hygroscopic material that undergoes dimensional changes when it experiences a change in moisture content. This phenomenon occurs on a local (fiber) scale. The dimensional change that occurs with changes in moisture content is due to drying or swelling forces in the wood. Dimensional changes in wood occur whenever there is a change in the distribution of internal (or external) stresses. The degree of moisture-induced-shrinkage (and consequently, shrinkage-related stress) depends on several known factors, such as galactan content, micro-fibril angle, specific gravity, MOE, and others. Many of these factors can be quantitatively or qualitatively evaluated with different types of sensors. For example, MOE can be estimated from the propagation of sound through wood, and specific gravity can be estimated from the capacitance of wood. The combined use of multiple sensors can then be used to estimate the moisture-induced shrinkage patterns in wood. The spatial resolution of the patterns depends on the spatial resolution of the measurements.

The extent of moisture-induced dimensional change for a given piece of wood depends on physical and chemical properties of the wood, as well as both the magnitude of the moisture change and the values of the initial and final moisture contents. The shrinkage behavior of wood is commonly expressed as a shrinkage-coefficient (alternatively called LSRC=Longitudinal Shrinkage Rate Coefficient); this is defined as $$LSRC = \frac{\Delta l/l}{\Delta MC}$$

where l is the length of the wood segment, MC is the moisture content of the wood, and the Greek letter Δ is the familiar mathematical difference operator. This shrinkage-coefficient is a function of the moisture content.

Estimation of shrinkage-coefficient patterns from multiple sensors may be achieved via a shrinkage-coefficient prediction equation and/or algorithm, as well as inputs from the sensors to the equation or algorithm. More than one shrinkage-coefficient prediction equation and/or algorithm may be utilized for each section of a wood product. The estimation of shrinkage patterns in a piece of wood can be determined from the appropriate shrinkage-coefficients and starting and ending moisture states.

The inputs to a shrinkage model are functions of the sensor signals and may be either quantitative or qualitative. For example, an input could be the estimated moisture content for each 12 inch lineal section of a piece of lumber, as estimated by a moisture meter. Another example is an indicator for the presence or absence of a knot in a 12 inch by 1 inch section of wood, based on an RGB image. Inputs to the models may be direct sensor measurements, pre-processed signals, or combined signals from several sensors. Signal pre-processing may include, but is not limited to, such steps as filtering, smoothing, derivative calculations, power spectrum calculations, Fourier transforms, etc., as is well known in the art.

The shrinkage-coefficient prediction equation(s) and/or algorithm(s) are used to map the set of inputs to a real-valued number. There are many forms of equations or algorithms that could be used, and a general reference is Hastie, et al[15]. A common example is a linear model of the form, $$y_j = \beta_0 + \sum_i \beta_{ij} x_{ij},$$

where $y_j$ is the response variable (e.g., LSRC) and the set of inputs $x_{ij}$ may be the inputs described above, or basis expansions of those inputs. Typically, the coefficients for such a model will not be known a-priori, and may be determined from a training-set of data. Other examples of supervised learning procedures include regression trees, additive models, neural networks, penalty methods, and boosting methods.

[15]Hastie, T., Tibshirani, R., and Friedman, J., (2001) The Elements of Statistical Learning, Springer, N.Y.

The spatial resolution of the inputs will determine the spatial resolution of the shrinkage estimates. If the resolution of the shrinkage estimates is high enough, it is possible to estimate shrinkage patterns throughout a piece of wood such as a board. In an embodiment, resolution required for a 2×4 piece of lumber may be 12 inches (long)×¾ inch (wide)×¾ inch (thick), although any practical level of resolution is possible. The section of board over which a prediction is made is a coupon. The pattern of coupon shrinkage estimates can be used to represent the shrinkage patterns in a wood product.

Two general types of shrinkage estimates may be used: 'absolute' shrinkage estimates which predict, for example, a shrinkage value for each coupon-level piece of a board; and 'differential' shrinkage estimates which predict a shrinkage difference between a coupon and a reference coupon.

Localized moisture content changes in wood may occur, for example, when there is a change in the ambient RH conditions, or when moisture-content non-uniformities in the wood are allowed to equilibrated. The estimated shrinkage patterns—either absolute or differential—can then be used to estimate the moisture-induced dimensional changes in the wood product. This could be accomplished, for example, by using the patterns of shrinkage estimates as inputs to a finite element model, although other options exist.

The following example illustrates how information from multiple sensors was used to estimate the dimensional change in wood due to a change in ambient relative humidity.

EXAMPLE 2

The sensor data used were "Tracheid-effect" line images and absorbance spectra obtained from near infrared (NIR) spectroscopy. (Additional information describing these two sensor technologies can be found in (Nystrom and Hagman)[16] and (Williams and Norris)[17] respectively). A training data set consisting of approximately 350 12"×1"× ¾" pieces of wood was used to build a shrinkage-coefficient calibration model. Each piece of wood was scanned for both Tracheid-effect images and NIR spectra. Several parameters were calculated from each Tracheid-effect image. In addition, each piece of wood was equilibrated at two different times in two different relative humidity environments—20% RH and 90% RH. Length measurements were made at each humidity condition and the moisture-induced dimensional change was recorded.

[16]Nystrom, J.; Hagman, O.; Methods for detecting compression wood in green and dry conditions, Proceedings of the SPIE—The International Society for Optical Engineering (1999) vol. 3826, p. 287-94.

[17]Williams, P., Norris, K. (editor), (2001) Near-Infrared Technology in the Agricultural and Food Industries, Second Edition, American Association of Cereal Chemists, St. Paul, Minn.), 312 pp.

Figure 4:
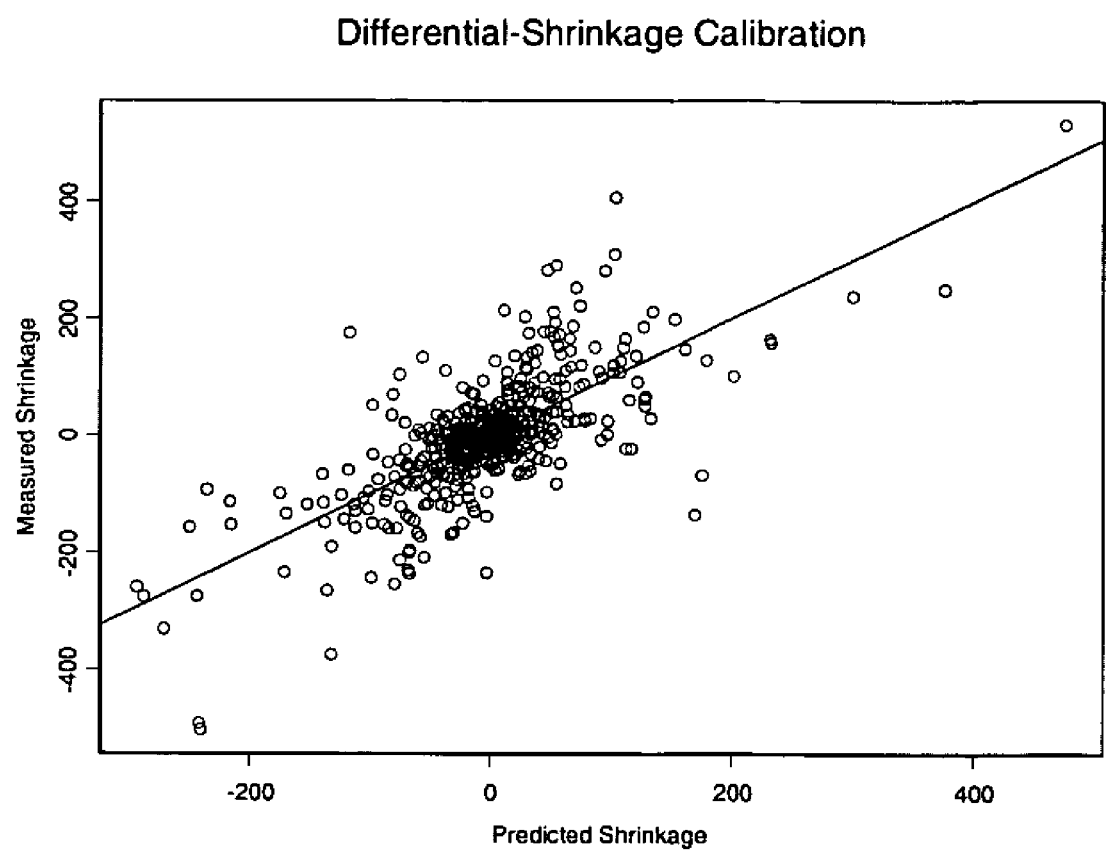
FIG. 4 is a calibration plot for a differential shrinkage-coefficient model in an embodiment of the present invention.

A prediction model for dimensional change was developed based on first-principle considerations using Tracheid-effect parameters and NIR spectra as inputs. The prediction equation used is $LSRC=\beta_0+\beta_1 \cdot D+\beta_2 \cdot R+\beta_3 \cdot R \cdot D$, where LSRC is the moisture-induced length-wise dimensional change of each piece of wood, the β's are regression coefficients estimated from the training dataset, D is the 'exponential decay' (rate of decay of the intensity as a function of distance from the projected light-source) of the tracheid-effect line intensity, and R is the ratio of two NIR absorbance values, A1700/A1650. The calibration plot for a differential shrinkage-coefficient model is shown in FIG. 4.

Figure 5:
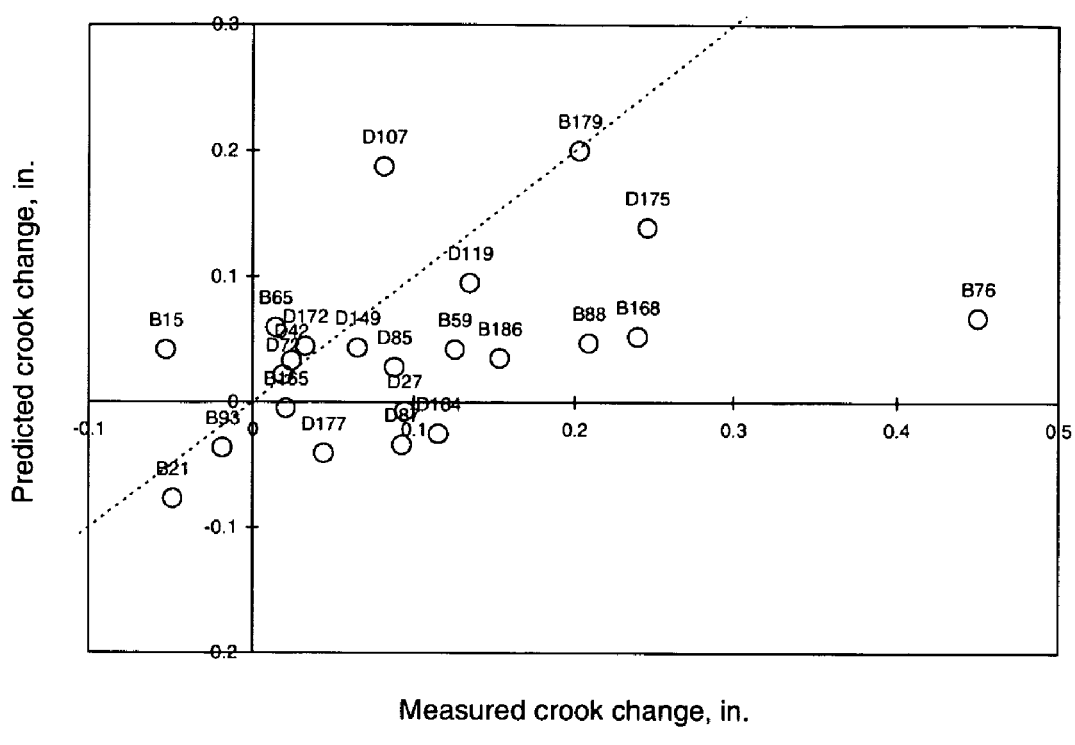
FIG. 5 is a plot of predicted change in crook against the measured change in an embodiment of the present invention.

Following the calibration of the shrinkage-coefficient model, 23 8-foot 2"×4" boards were scanned for both tracheid-effect images and NIR spectra. These pieces of wood had already been cycled through two relative humidity environments, and the change in crook and bow were recorded on each piece. The parameters calculated from the tracheid-effect and NIR data were used as inputs to the differential shrinkage-coefficient model to produce a map of differential shrinkage-coefficient values for each piece of lumber. A shrinkage map was calculated from the shrinkage-coefficient estimates and the target moisture contents. The shrinkage map was then input to a finite element model (DIMENS) to predict the change in warp-profile of each piece of lumber. The predicted change in crook is plotted against the measured change in FIG. 5.

The previous example illustrates the prediction of moisture-induced crook-change from estimated shrinkage maps using a finite element model. Similar methods can be used for cup and bow. Analogous methods can be used to predict moisture-induced twist from estimated grain-angle, pith location and possibly other variables.

Residual stress arises only in the presence of shrinkage differences, noting that uniform shrinkage is an indication of no residual stress present in a sample. Thus, it is proposed that there should be a strong relationship between residual longitudinal stress and longitudinal shrinkage differences, rather than between residual longitudinal stress and longitudinal shrinkage itself. This requires a scan for residual stress when the nearby shrinkage is different, not just when the local shrinkage is relatively high.

During the manufacture of lumber, it is sometimes desired to rip a piece in order to generate 2 or more narrow pieces whose combined value is greater than the wider parent. If there are residual stresses in the parent board, those stresses might be relieved during this ripping operation causing the ripped pieces to spring outward and undergo added undesirable warp distortion. Thus, there is a need to understand whether or not this potential exists in a parent piece of lumber before a rip decision is made. Estimates of longitudinal shrinkage patterns can be used for this purpose as illustrated by the following example.

EXAMPLE 3

Eighteen 2×4 cross sections were equilibrated to 20% RH and ripped into four equal coupons. The instantaneous strain of each coupon was determined from the difference in length before and after ripping. A longitudinal shrinkage rate coefficient (LSRC) was also determined for each coupon. Two pairs of coupons on either side of centerline were reviewed. Data from these pairs was analyzed to determine whether predicted LSRC differences (based on methods described earlier) could be used to identify pairs having high instantaneous strain difference (i.e. sections likely to distort during a ripping operation.)

Results are shown in FIG. 21. The test demonstrated that LSRC estimates can indeed be used to identify pieces of lumber that likely contain significant internal stresses and are, therefore, not candidates for a ripping operation.

The method can be applied to a board that has residual moisture gradients resulting from kiln-drying and that will subsequently change shape as the internal moisture equilibrates both within the piece (moisture leveling) and to its external environment. If the subsequent shape change is large enough, such a board may no longer meet the warp limits for its designated grade.

Shape change may be predicted according to the above method using the predicted shrinkage-coefficients for each coupon within the board, together with the anticipated moisture content change of each coupon. If the final state is one of uniform, equilibrated moisture content, then the moisture content changes of the coupons will not all be the same if there initially are moisture gradients within the board. In the method, the moisture content change for each coupon may be determined from the initial moisture content distribution and the final target moisture content. The moisture content change is then multiplied by the corresponding longitudinal shrinkage rate coefficient determined for the coupon. The resulting coupon shrinkage values are processed using, for example, a finite-element and/or an algebraic warp prediction model to determine the anticipated warp changes due to leveling and equilibration of the initial moisture gradients. The predicted warp changes are finally added to the initial warp values of the board to determine whether or not the final shape of the piece will exceed any of the warp limits for its designated grade.

An example of the above-described method is provided below:

EXAMPLE 4

Figure 6:
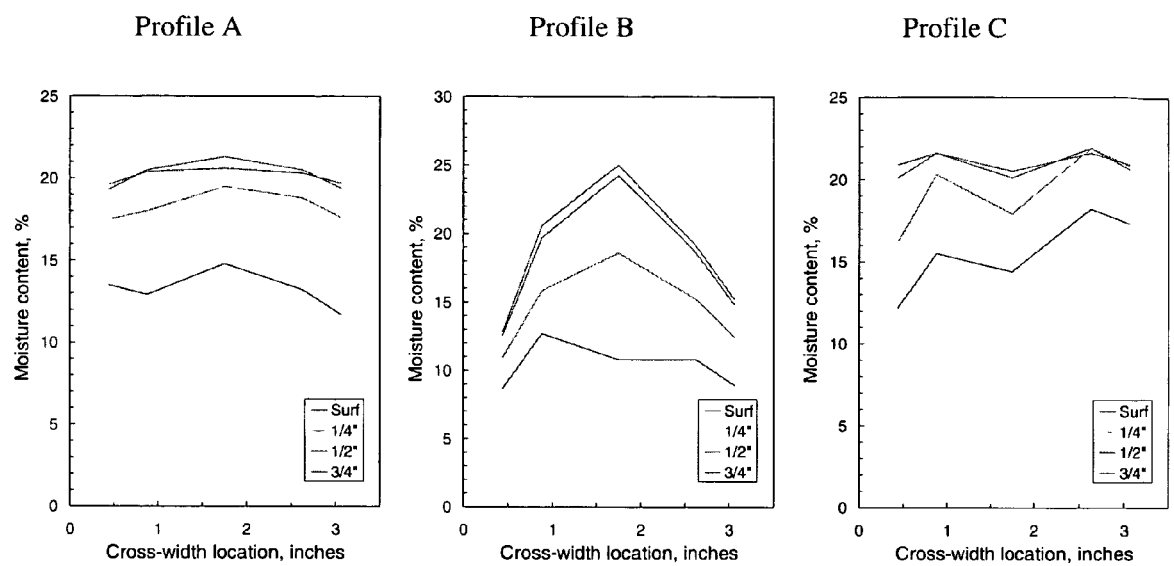
FIG. 6 is a chart of different initial moisture content profiles.
Figure 7:
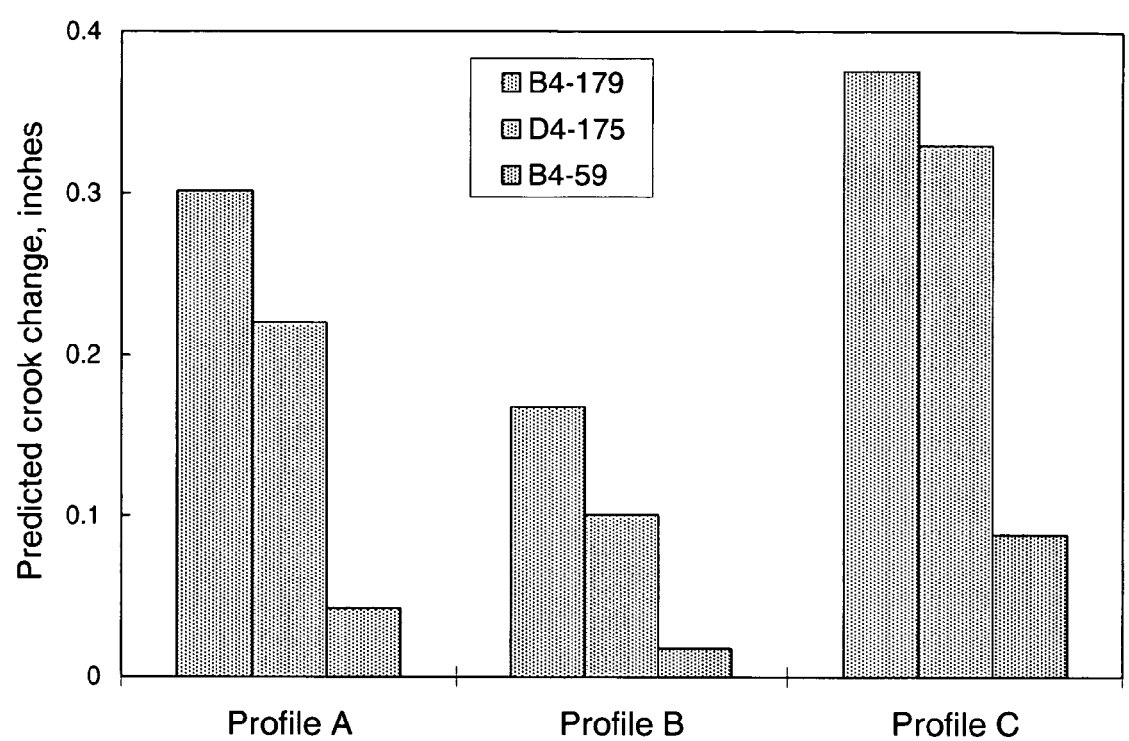
FIG. 7 is a chart of predicted crook changes for each profile in FIG. 6.

The anticipated crook changes of three 8-ft. 2 inch×4 inch boards (B4-179, D4-175, and B4-59) were determined for several different hypothetical moisture content leveling and equilibration scenarios. Three different initial moisture content profiles, as previously measured in kiln-dried lumber, were used and the final equilibrium moisture content was assumed to be 12%. The longitudinal shrinkage rate coefficients of the coupons within the three boards were determined using the above-described methods. FIG. 6 illustrates different initial moisture content profiles and FIG. 7 illustrates predicted crook changes for each profile. The predicted crook change for each board is added to its actual crook at its initial moisture content condition in order to determine whether or not the crook at the final moisture content condition would exceed the crook limit for the designated grade of the board.

Figure 8:
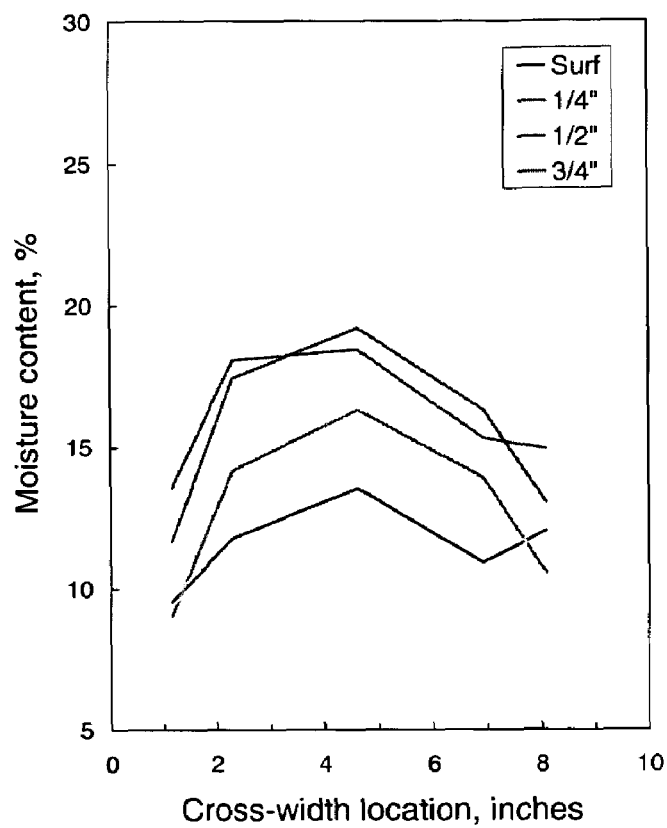
FIG. 8 is a plot of moisture content profiles at different depths.

B. Methods of Combining Measurements of Surface Moisture Patterns with a Measurement of Bulk (Average) Moisture to Estimate Moisture Gradients and Patterns Within a Wood Product At the end of kiln drying, the moisture content in each piece of lumber is typically distributed in a non-uniform manner, with relatively higher moisture contents near the core of the piece and lower moistures at and near the surfaces. This activity is illustrated in FIG. 8. Such patterns may not be symmetric in cross-section, with edge-to-edge and face-to-face differentials. The patterns may vary along the length of the board, typically with relatively lower moisture contents near each end. Prior testing has shown that such moisture patterns persist in the lumber for weeks after drying, and thus will often remain at the time of planing.

Because of such moisture variability, board warp profile predictions of the kind described above may require an estimate of the moisture content of each shrinkage coupon. These estimated moisture content values may be used together with the specified final target moisture content to determine the moisture content changes for which the warp change of the board must be predicted.

At any location along the length of a board, the surface moisture content profile and the corresponding average moisture content may be combined to obtain an estimate of the moisture content for each shrinkage coupon in that length section. An estimated moisture content is determined for each shrinkage coupon position using a linear model that employs the average moisture content of the corresponding board section (for example, from an NMI meter) and the surface moisture content for that coupon position (for example, from an electrical-resistance pin-type moisture meter). The moisture content estimate model is of the general form:

$$MC_{ij} = k0_i + k1_i * A_j + k2_i * S_{ij}$$

where $MC_{ij}$ is the estimated moisture content of the "i"th shrinkage coupon in the "j"th board section (generally there would be 8 coupons per section)

k values are constants but may have different values for each shrinkage coupon position "i"

$A_j$ is the average moisture content of the "j"th section $S_{ij}$ is the surface moisture content of the "i"th shrinkage coupon in the "j"th board section.

In general, there would be a different set of k values associated with each board width.

Figure 9:
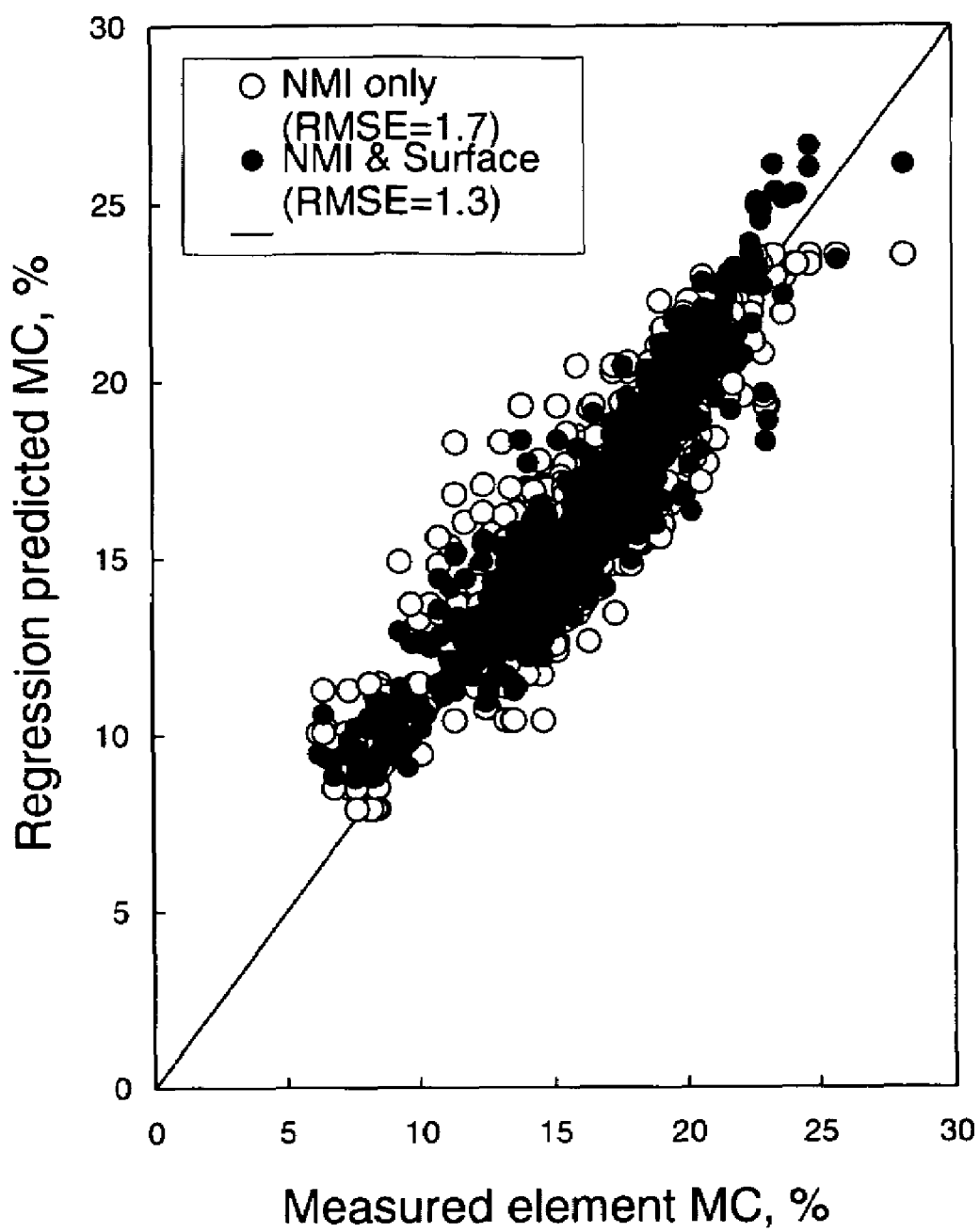
FIG. 9 is a plot of predicted moisture content for a wood product in an embodiment of the present invention.

FIG. 9 illustrates results from a test of the claimed method. In that test, it was shown that when combining both the average moisture content and the surface moisture content pattern, the error of the prediction of coupon (element) moisture content was reduced from 1.7% to 1.3% mc (RMSE), as compared to predictions based on the average moisture content alone.

Near Infrared (NIR) absorbance spectroscopy techniques can be used to measure the moisture content of materials. There are many examples known to those skilled in the art demonstrating the basic method for many biological materials, including wood. In most examples, the material is ground and thus relatively homogeneous with the surface and interior having similar moisture contents.

In wood this may not be the case. Water has several absorption bands in the NIR region. Due to the strength of these absorption bands and the optical density of wood, the NIR reflectance spectrum at the water absorption bands is a measure of the surface moisture (within a few millimeters of the surface). If full NIR spectrum methods are used, a single NIR reflectance spectrum can be used in both surface moisture and shrinkage prediction models. If discrete wavebands, or ratios of discrete wavebands, are used, then it is likely that the NIR wavebands selected for surface moisture prediction models will be different from those used to model shrinkage.

The most common NIR models for moisture are multiple linear regression models of second derivative spectra at a few (typically three or less) wavebands. However, full spectrum models, or models using ratios of absorbance values or ratios of derivative values can also be used. Using these methods, NIR spectral data are analyzed to determine and assign a surface moisture content for each shrinkage coupon.

The amount of light absorbed by water varies from water absorbance band to band. In general, the longer the wavelength the more light that is absorbed for the same water content. Thus, by selecting the wavelength for water measurement, one can control to some degree the depth of penetration of the light into the material. Thus, there would be more penetration into the wood at the 960 nm water band than at the 1910 nm water band. If one was interested in the surface moisture content, then longer wavebands like 1910 nm should give a measure closer to the surface, while 960 nm should give an average moisture content to a greater depth. Such measurements may be taken by, for example, devices or systems such as a Kett High Moisture NIR meter (model number KJT100H) manufactured by Kett Corporation.

A number of the bulk properties of wood are affected by its moisture content. For example, below the fiber saturation point, both the modulus of elasticity (MOE) and the electrical resistance increase with decreasing moisture content. Such relationships form the basis for a variety of moisture measurement methods including, for example, dielectric, electrical resistance, and nuclear magnetic resonance. These methods are employed in various commercial lumber moisture measurement systems, such as those made by Wagner and NMI (dielectric), and by Delmhorst (electrical resistance). In both the Wagner and NMI planer moisture meters, the lumber passes over a capacitance-measuring plate and the average, or bulk, moisture content of the wood in the measurement zone is determined by its dielectric properties. Such state-of-the-art planer moisture meters are not yet able to resolve the cross-sectional variability in moisture content with a resolution on the order of the shrinkage coupon dimensions. They provide a cross-sectional average moisture content that is characteristic of a short length section of the board. That average moisture content can be used with an NIR-based estimate of moisture content variation over the surface of the board to estimate the moisture gradients and patterns within the board, following the above-described method.

C. Methods of Estimating the Dimensional Stability of a Wood Product from Simple Algebraic Differences in Moisture, Shrinkage Rates and Grain Angles Observed on Outer Surfaces Finite-element modeling of lumber warp behavior has shown that crook and bow stability are governed almost entirely by the pattern of variation in the lengthwise shrinkage within the piece. Specifically, differentials in lengthwise shrinkage across the width largely determine crook, while differentials across the thickness are responsible for bow. Furthermore, it has been discovered that the quantitative relationship between crook or bow stability and lengthwise shrinkage can be established using relatively simple mathematical operations, rather than more sophisticated and complicated finite-element modeling methods. In particular, the curvature of any board length-segment or section, expressed as the second derivative of the crook or bow profile, can be determined from a linear combination of the shrinkage values of the coupons comprising that segment or section. The overall crook or bow profile of the board can be determined from a section-by-section double-integration of those second derivative values.

To determine crook, each board segment must be divided into at least 2 shrinkage coupons across the width. In general, better results may be obtained when each board segment is divided into at least 4 coupons across the width. If a board segment is divided into four shrinkage coupons, having shrinkage values T1, T2, T3, and T4, then the crook resulting from that shrinkage will exhibit a curvature over that segment (expressed as the second derivative of the board's edge profile) that can be determined by a linear combination of the general form:

$$C''=k1(T1-T4)+k2(T2-T3)+k3$$

where $C''$ is the second derivative of the crook profile along the edge of the board k values are constants but may have different values for each board width T values are coupon shrinkage values that are determined by the product of the corresponding longitudinal shrinkage rate coefficient (LSRC) and moisture content change (MC):

$$Ti = LSRCi \times MCi$$

This method was tested in the following example:

EXAMPLE 5

Figure 10:
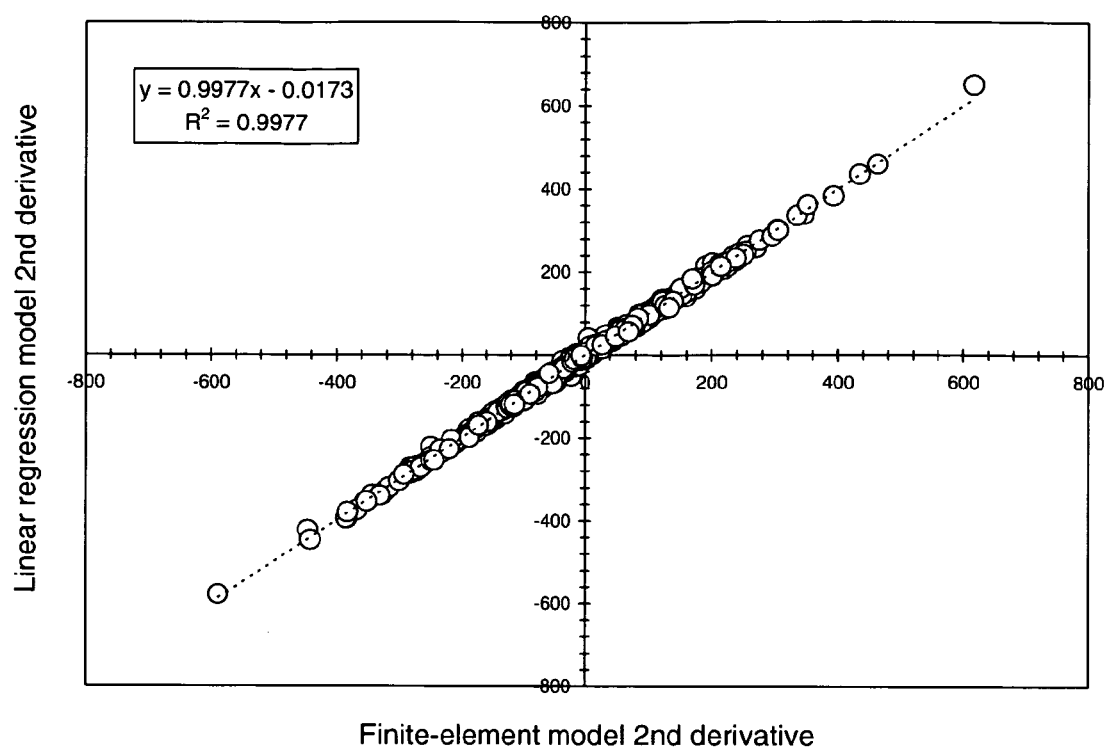
FIG. 10 is a plot comparing the second derivative values calculated using a method of the present invention with the corresponding second derivative values calculated from the crook profiles predicted by the finite-element model.

Finite-element model predictions were made for crook in 138 different examples of 8-ft. 2×4 boards. Each of these example boards was divided into 6 length segments and each length segment was divided into 8 shrinkage coupons, using a 4×2 configuration, namely, with four coupons across the width by two coupons through the thickness. The shrinkage values for each pair of coupons at each width location were averaged to give four shrinkage values across the width, per the above equation. The second derivative of the predicted crook profile was calculated for each board segment, and a least-squares regression was used to determine the coefficients (k) in the equation above. FIG. 10 illustrates a plot comparing the second derivative values calculated using that equation (C") with the corresponding second derivative values calculated from the crook profiles predicted by the finite-element model, and shows excellent agreement.

Figure 11:
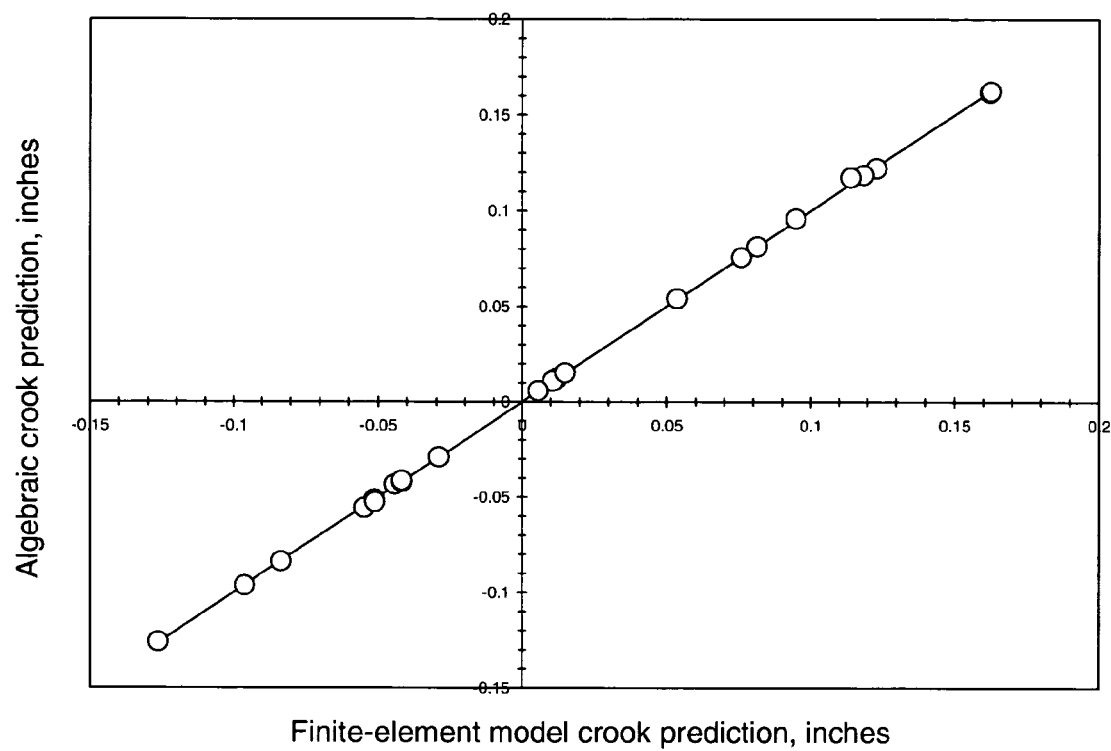
FIG. 11 is a plot of crook values calculated using a method of the present invention compared to corresponding crook values predicted using a finite-element model.

To predict the crook of a board, the second derivative values calculated using the above equation (C") are integrated twice to yield the actual edge profile of each board segment. This method was tested using coupon longitudinal shrinkage rate coefficients determined for 23 8-ft. 2×4 boards. First, the second derivative values for each length segment were calculated using the above equation, then those derivative values were integrated twice to determine the crook profile of each of the 23 boards. The resulting crook values are compared to the corresponding crook values predicted using the finite-element model, and show excellent agreement in FIG. 11.

To determine bow, each board segment must be divided into at least 2 shrinkage coupons through the thickness. If a board segment is divided into two shrinkage coupons, having shrinkage values T1 and T2, then the bow resulting from that shrinkage will exhibit a curvature over that segment (expressed as the second derivative of the board's face profile) that can be determined by a linear combination of the general form:

$$B''=k1(T1-T2)+k2$$

where
- B" is the second derivative of the bow profile along the face of the board
- k values are constants but may have different values for each board width
- T values are coupon shrinkage values that are determined by the product of the corresponding longitudinal shrinkage rate coefficient (LSRC) and moisture content change (MC):

$$Ti=LSRCi \times MCi$$

This method was tested in the following example:

EXAMPLE 6

Figure 12:
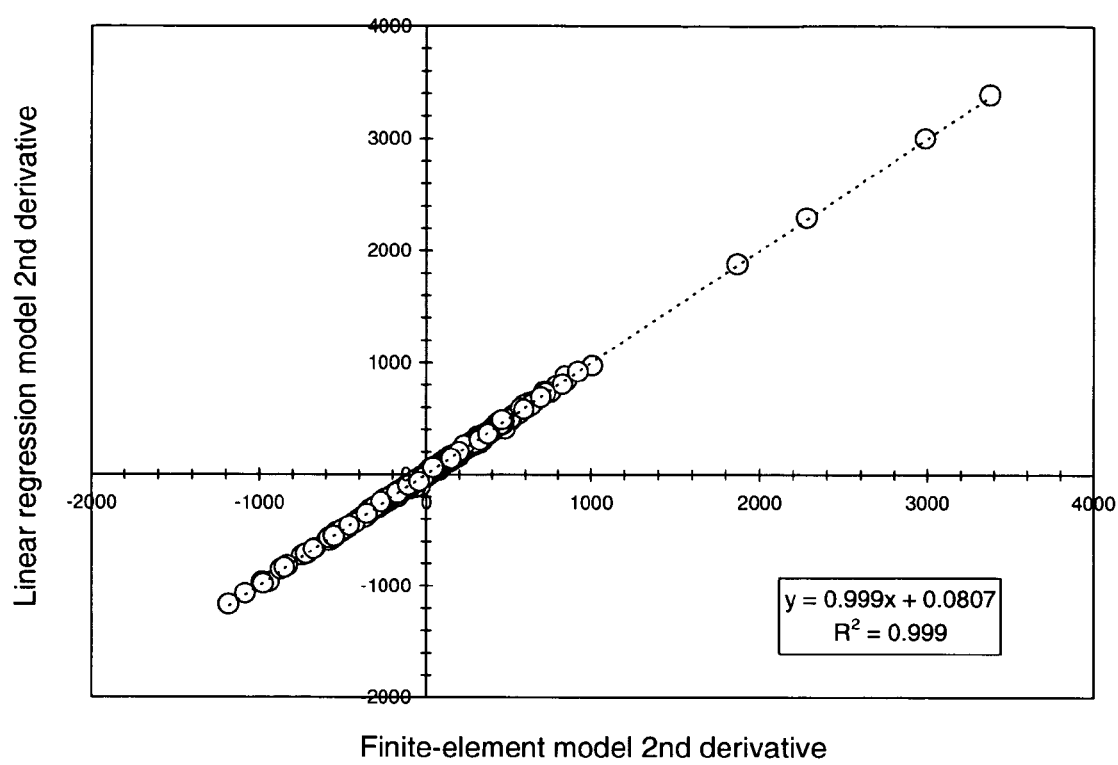
FIG. 12 is a plot comparing second derivative values calculated using a method of the present invention with corresponding second derivative values calculated from bow profiles predicted by a finite-element model.

Finite-element model predictions were made for bow in 138 different examples of 8-ft. 2×4 boards. Each of these example boards was divided into 6 length segments and each length segment was divided into 8 shrinkage coupons, using a 4×2 configuration, namely, with 4 coupons across the width by two coupons through the thickness. The shrinkage values for each set of 4 coupons at each face were averaged to give two shrinkage values through the thickness, per the above equation. The second derivative of the predicted bow profile was calculated for each board segment, and a least-squares regression was used to determine the coefficients (k) in the equation above. The plot in FIG. 12 compares the second derivative values calculated using that equation (B") with the corresponding second derivative values calculated from the bow profiles predicted by the finite-element model, and shows excellent agreement.

Figure 13:
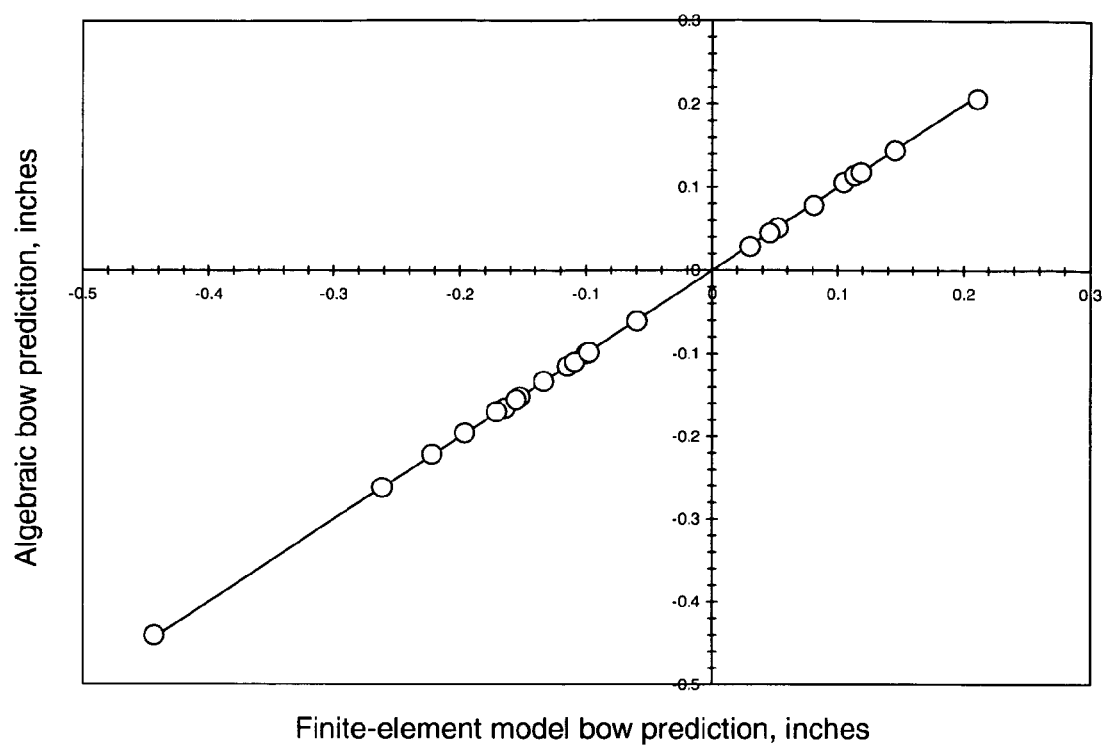
FIG. 13 is a plot of bow values calculated using a method of the present invention compared to corresponding crook values predicted using a finite-element model.

To predict the bow of a board, the second derivative values calculated using the above equation (B") are integrated twice to yield the actual face profile of each board segment. This method was tested using coupon longitudinal shrinkage rate coefficients determined for 23 8-ft. 2×4 boards. First, the second derivative values for each length segment were calculated using the above equation. Then, those derivative values were integrated twice to determine the bow profile of each of the 23 boards. The resulting bow values are compared to the corresponding bow values predicted using the finite-element model, showing excellent agreement in FIG. 13.

D. Methods of Estimating the Shrinkage and Grain Angle Properties of Wood by Interpreting the Intensity Pattern that is Diffusely Reflected from a Surface Illuminated by a Light Source (Laser or Non-Laser)

The tracheid-effect in wood is known (see, for example Nystrom, 2003). When a wood surface is illuminated by a point or line light source, the patterns of diffuse reflectance are influenced by the physical and chemical properties of the wood. Metrics or parameters calculated from these patterns may be used to estimate physical properties of the wood, such as, for example, shrinkage and grain-angle properties.

Figure 14:
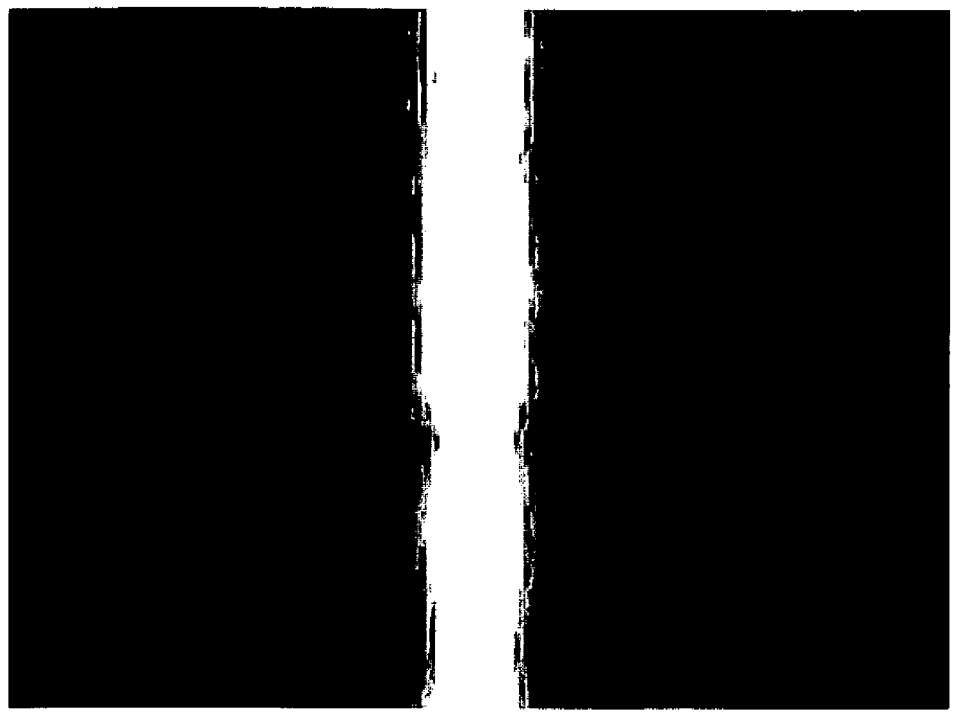
FIG. 14 is an example of a grayscale image from a line-light-source projected onto a wood product.

Many types of parameters may be calculated from the diffuse reflectance patterns. When the diffuse-reflectance is focused to an area array camera, the grayscale pattern of the resulting image may be analyzed with standard or non-standard image analysis techniques, as is well known in the art. An example of a grayscale image from a line-light-source is shown in FIG. 14. Examples of some standard image analysis metrics include size of area formed between two grayscale thresholds, and convex hull area of an image.

Figure 15:
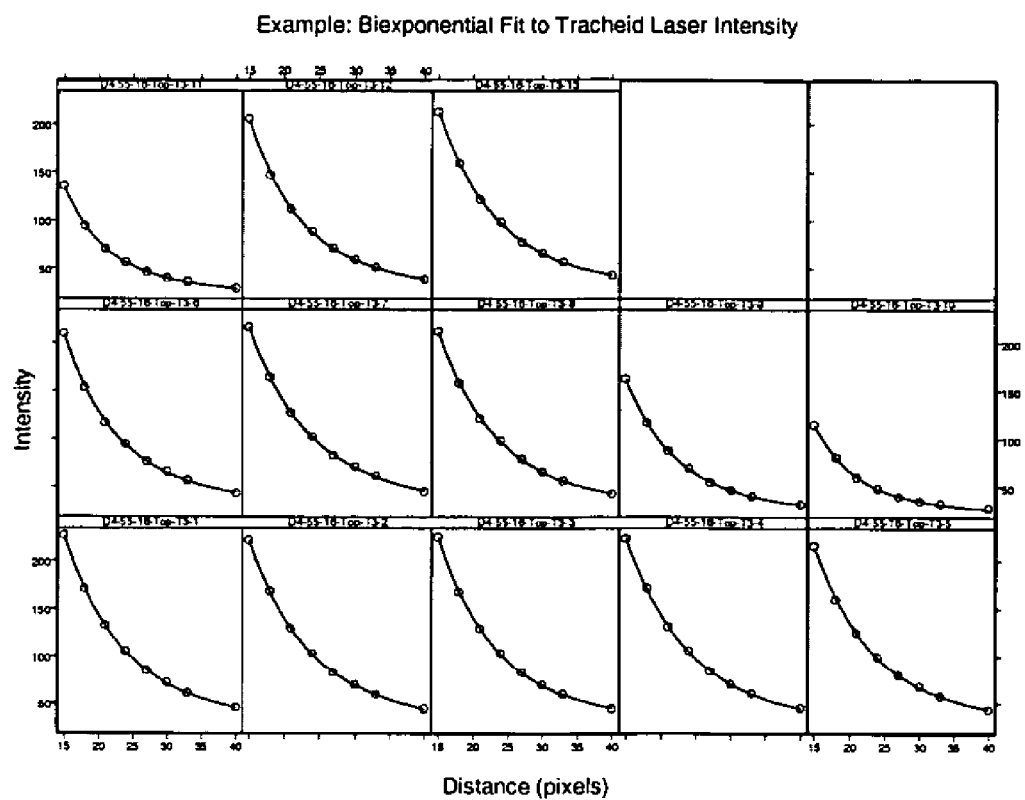
FIG. 15 provides several examples of a bi-exponential model fit to tracheid-effect line images.

Statistical and mathematical parameters may also be calculated from patterns of diffuse reflectance. For example, the rate of decay of the intensity as a function of distance from the projected light-source may relate to the dimensional stability of wood. There are many different models for estimating the rate of decay. A common model is log (intensity)=A+kx, where x is the distance from the projected light source, and A and k are model parameters. Examples of other models are described in Bates and Watts, 1988. It has been empirically noted that the rate of decay of diffusely reflected light intensity may be represented by a combination of exponential-decay processes. The bi-exponential process can be represented by the equation: $E(y_i)=\phi_1 \exp(-\phi_2 x_i)+\phi_3 \exp(-\phi_4 x_i)$, $\phi_2 > \phi_4 > 0$. The estimated parameters from the exponential decay processes may reflect different wood properties and could each be used as inputs to a shrinkage model. FIG. 15 shows several examples of the bi-exponential model fit to tracheid-effect line images.

Parameters, such as those related to the rate of decay of light intensity, may be estimated on either 'side' of the light image or by combining information from each side. Empirical evidence also suggests that a comparison of decay rates on the 'left' and 'right' side of a light source may provide useful predictive information.

When the light source is a spot, other parameters may be computed from the diffuse reflectance patterns. A spot light source typically makes an ellipse pattern on the surface of wood. Parameters such as the ellipse ratio, ellipse orientation, and ellipse angle may be calculated, as discussed in (Zhou and Shen, 2002). The surface grain angle may be estimated from the ellipse angle.

The physical properties of wood that influence the tracheid-effect may be local in nature. The spatial resolution of estimates based on the calculated parameters will then depend on the frequency of sampling the light intensity patterns. The various attributes computed from the intensity patterns can be used as inputs to a shrinkage prediction equation or algorithm. Such an equation maps the set of inputs to a real-valued number. There are many forms of equations or algorithms that could be used, and a general reference is Hastie, et al. The following example illustrates how information from a laser line image was used to estimate longitudinal shrinkage rate coefficients of wood:

EXAMPLE 7

A training dataset consisting of approximately 350 12"× 1"×¾" pieces of wood was used to build a shrinkage-coefficient calibration model. Each piece of wood was scanned with a Tracheid-effect line image and a side-spot image. Several parameters were calculated from each Tracheid-effect image. In addition, each piece of wood was equilibrated at two different times in two different relative humidity environments—20% RH and 90% RH. Length measurements were made at each humidity level and the moisture-induced length change was recorded.

Figure 16:
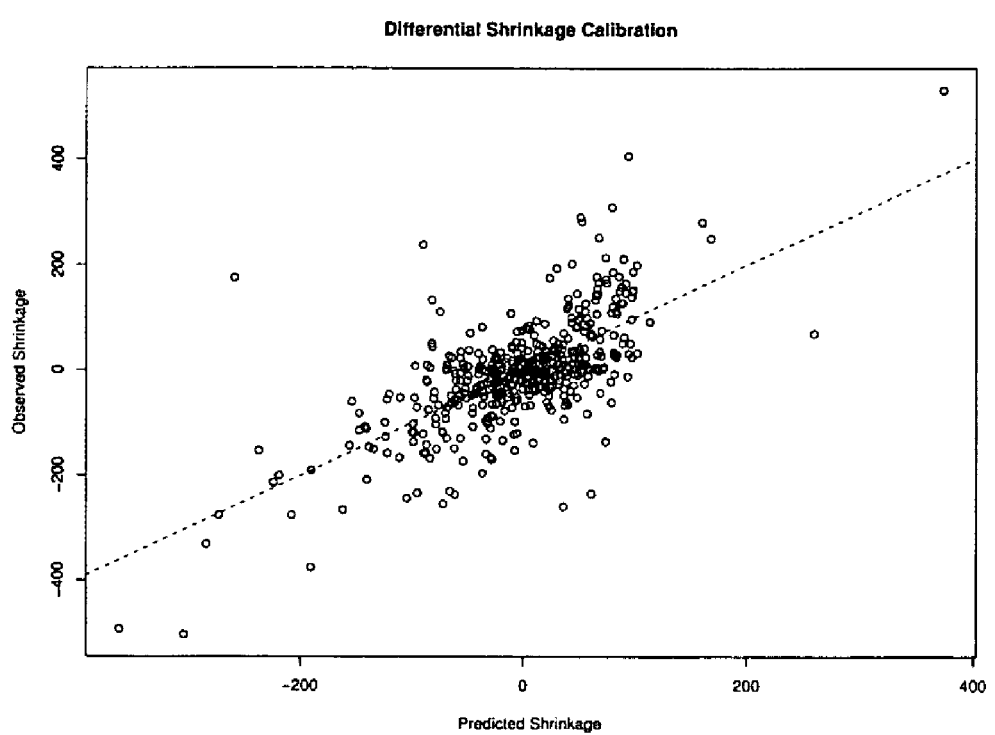
FIG. 16 is a calibration plot for a differential shrinkage-coefficient model.

A prediction model for dimensional change was developed using tracheid-effect parameters as inputs. The prediction equation was constructed using multivariate-adaptive-polynomial-spline-regression. Five main terms were included in the model: 'Right' decay parameter, mean Ellipse ratio, convex-hull-area-height, mean-angle, and the within-piece standard deviation of the ratio of the 'right' and 'left' decay parameters. In addition, 3 spline-knots and the interaction between 'right' decay and mean-angle were included in the model. The calibration plot for a differential shrinkage-coefficient model is shown in FIG. 16.

The previous example illustrated the prediction of wood shrinkage-coefficients from parameters calculated from both line-intensity and spot-intensity images. Analogous methods can be used to predict grain-angle from both line and spot images.

E. Methods of Using Multiple Sensors (Sensor Fusion) to Infer Crook and Bow Directly Crook and bow result from dimensional instability in a piece of wood. Many factors are known to be associated with the dimensional stability of wood. For example, wood with high MOE is generally dimensionally stable, while wood with large amounts of compression-wood is typically unstable and prone to crook or bow. Moisture-induced dimensional instability is a result of moisture-induced shrinkage patterns in a wood product, such as a piece of lumber. One approach to estimating dimensional change, discussed above and illustrated in Example 2, first estimates the shrinkage-coefficient patterns in a piece of wood, then uses these shrinkage-coefficient patterns to predict crook or bow resulting from a change in moisture content using, for example, a finite element model. This can be thought of as a two-step approach to warp prediction wherein a first step is to predict shrinkage, and a following step is to predict warp.

Another approach is to directly predict the crook or bow of a piece of wood using data from multiple sensors and a single prediction model or algorithm. Using this approach, the prediction model or algorithm may use inputs of many different resolution scales. The model inputs are functions of the sensor signals and may be either quantitative or qualitative. For example, an input could be the estimated average moisture content for the entire piece of wood, as estimated by a moisture meter. Another example is an indicator for the presence or absence of a knot in a 12" by 1" section of wood, based on an RGB image. Inputs to the models may be direct sensor measurements, pre-processed signals, or combined signals from several sensors. Signal pre-processing may include, but is not limited to, such steps as filtering, smoothing, derivative calculations, power spectrum calculations, Fourier transforms, etc., as is well known in the art.

The crook or bow prediction equation(s) and/or algorithm(s) are used to map the set of inputs to a real-valued number. There are many forms of equations or algorithms that could be used, and a general reference is Hastie, et al. Typically, the model or algorithm parameters will not be known a-priori, and must be determined from a training-set of data. The following example illustrates how information from multiple sensors was used to directly estimate the dimensional change in wood due to a change in ambient relative humidity.

EXAMPLE 8

Figure 17:
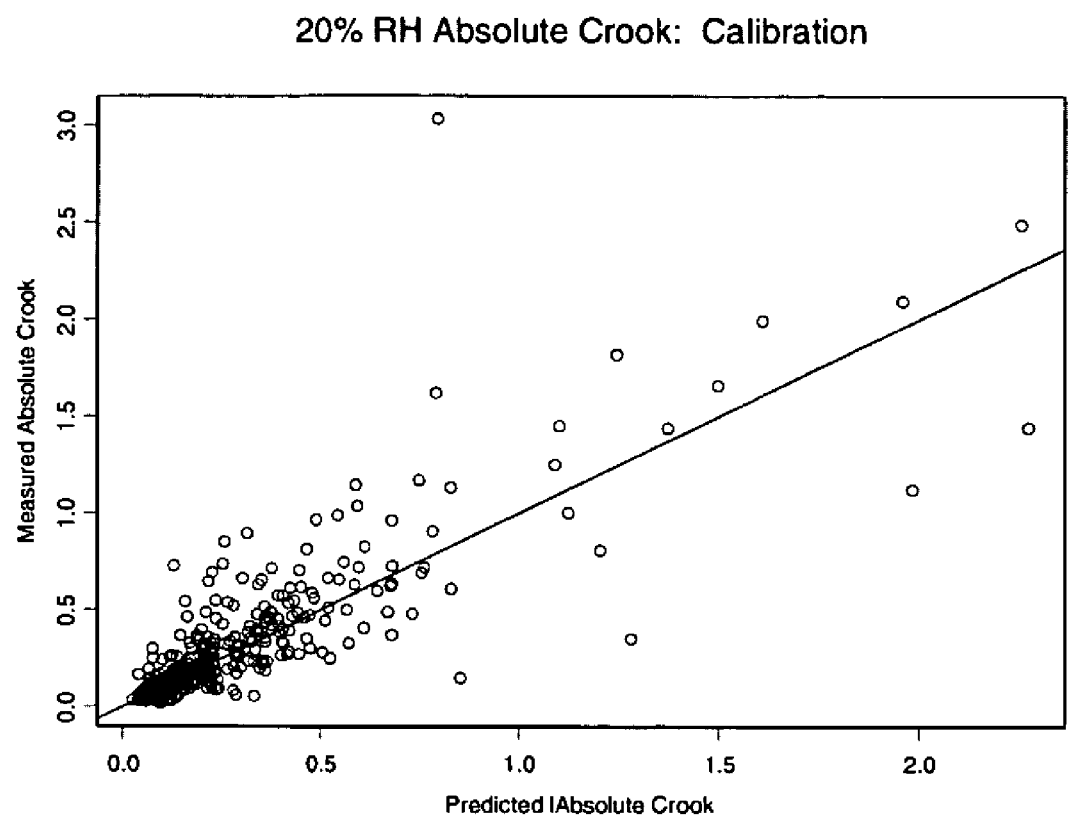
FIG. 17 is a calibration plot for absolute-crook at 20% RH.

Three units of lumber, each containing approximately 200 8-foot 2×4 boards were obtained from a mill. Each piece of lumber was measured at the mill for crook, bow, average moisture content, acoustic velocity and specific gravity. Each piece of wood was then placed in a 20% RH environment for 5 weeks and then measured again for crook and bow. In this example, the objective was to estimate the final crook or bow (at 20% RH) using the initial data from multiple sensor groups. Three inputs were used to develop an absolute-crook prediction model: initial absolute crook, acoustic velocity, and initial moisture content. A simple linear regression model with these inputs was trained on two units of lumber. The calibration plot for absolute-crook at 20% RH is shown in FIG. 17.

F. Methods of Rapidly Simulating "In-Service" Warp Distortion of a Wood Product and/or Rapidly Estimating Shrinkage Properties of a Wood Product by Using Electromagnetic Energy to Dry and Redistribute Absorbed Water Hygroscopic materials, such as wood, absorb or release an amount of moisture needed to reach equilibrium with the surrounding environment. Consequently, most wooden materials will undergo significant moisture change between the time they are manufactured and when they reach final equilibrium after put into service. Typical interior equilibrium moisture levels in the United States vary by geography and season with average values ranging from 6% in the desert Southwest to 11% along the Gulf Coast. (*Wood Handbook*[2]). Once wood is placed in a new environment it takes approximately 6 weeks to reach a new equilibrium moisture condition. Until that equilibrium state is reached, moisture gradients exist from the inside to the outside of a piece of wood.

An objective of the present invention is to predict how straight an individual piece of lumber will be after it reaches a final equilibrium state, i.e., where no moisture gradients exist. This prediction relies on estimating lengthwise shrinkage patterns within the piece of lumber and then interpreting how those shrinkage patterns interact to cause warp. In order for this technology to be applied, quality control procedures may be required to ensure that the "in service" warp prediction is accurate. Such procedures must be capable of providing rapid feedback on the accuracy of estimates of both shrinkage-coefficients and resulting distortion. The long time required for a wooden piece to reach moisture equilibrium presents a problem to the development of operationally feasible quality control methods. To resolve this problem, it is proposed to utilize electromagnetic energy to accelerate the rate at which a wood product reaches a new equilibrium moisture.

Electromagnetic energy is efficiently absorbed by polar molecules such as water. When wood is placed in a microwave or radio frequency field, the energy is preferentially absorbed by regions having higher moisture. As a result, water in these high absorbing regions rapidly migrates to lower moisture regions, thereby leveling the moisture gradients. This process can, therefore, be used on wood to quickly achieve a new moisture state that emulates in-service equilibrium in which moisture gradients are minimized.

This method can be used to validate both shrinkage-coefficient predictions and warp of full size pieces. The method can be used to emulate shrinkage or in-service distortion resulting from moisture leveling or moisture loss. To emulate distortion resulting from moisture leveling, the piece must be wrapped in a moisture barrier before it is placed in an electromagnetic field. Electromagnetic energy in the frequency range of, for example, 13.6 MHz (RF) to 2.45 GHz (microwave) can be used in this method. This full range can be used to accelerate the process of determining shrinkage-coefficients of small samples (less than 50 cubic inches); whereas the RF portion of the spectrum is preferred for inducing warp in full size lumber samples. In an embodiment, the wood product is dried to a moisture content which is less than 20%.

In an embodiment, a method is provided for confirming a warp distortion prediction (i.e., quality control) for a wood product. The method comprises the steps of: obtaining an initial moisture pattern for the wood product; predicting warp distortion of the wood product based on the initial moisture pattern; placing the wood product in an environment wherein the wood product is subject to electromagnetic energy; applying sufficient electromagnetic energy to the wood product to change its moisture content to a second level wherein the moisture content has a second value equivalent to an expected long term in-service equilibrium value; measuring warp distortion of the wood product at the second moisture level; and comparing the predicted warp distortion to the warp distortion at the second moisture level.

The following example describes an experiment conducted to compare longitudinal shrinkage rate coefficients determined by RF drying compared to conventional conditioning in a controlled environment:

EXAMPLE 9

A set of candidate wood specimens was equilibrated (size approximately ½" thick×1" wide×12" long) in 65% relative humidity for at least 3 weeks. 30 representative samples were selected from the equilibrated group. The weight and length of each specimen were measured. Each specimen was dried to approximately 5% moisture using RF dryer (drying done on approximately 5 minute cycle using a 20 KW 40 MHz dryer at Radio Frequency Company, Millis Mass.). The weight and length of each specimen was re-measured. The acquired data is used to estimate longitudinal shrinkage rate coefficients ($LSRC_1$) using the formula:

$LSRC_1$=length change÷initial length÷moisture content change

Figure 18:
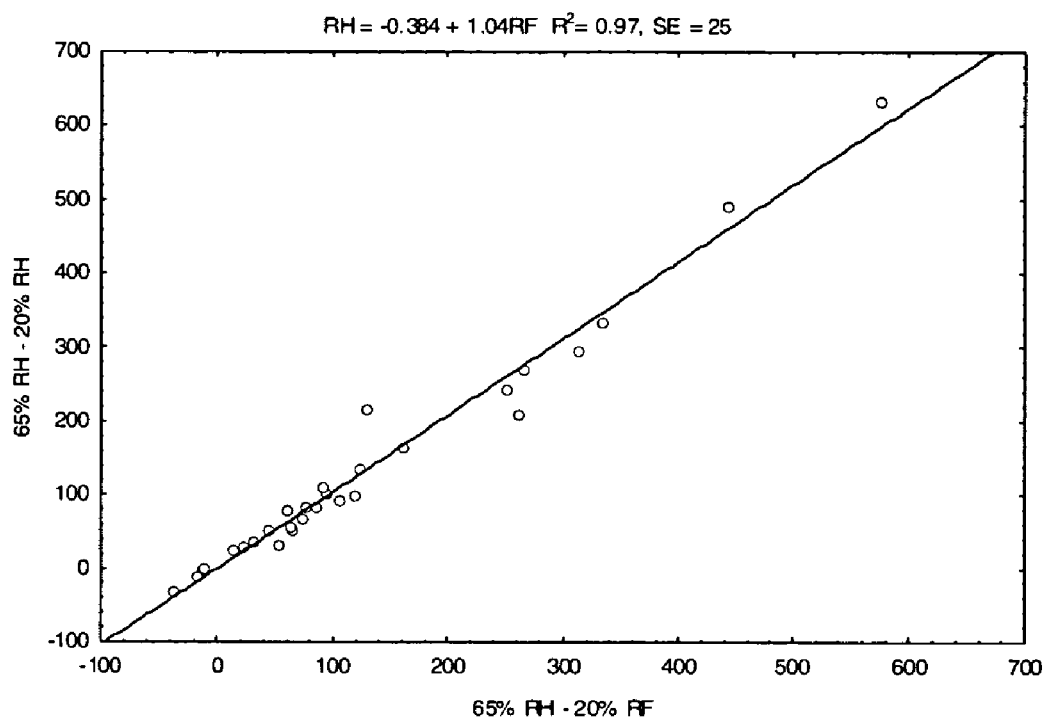
FIG. 18 is a plot of a comparison between shrinkage-coefficient estimates.

Next, the RF dried coupons were re-conditioned in 20% RH. The weight and length of each specimen were re-measured. This data was used to re-estimate longitudinal shrinkage rate coefficients ($LSRC_2$). A comparison was made between shrinkage-coefficient estimates $LSRC_1$ and $LSRC_2$. The results are plotted in FIG. 18 and show excellent agreement between the conventional and accelerated methods of estimating shrinkage-coefficients.

Figure 19:
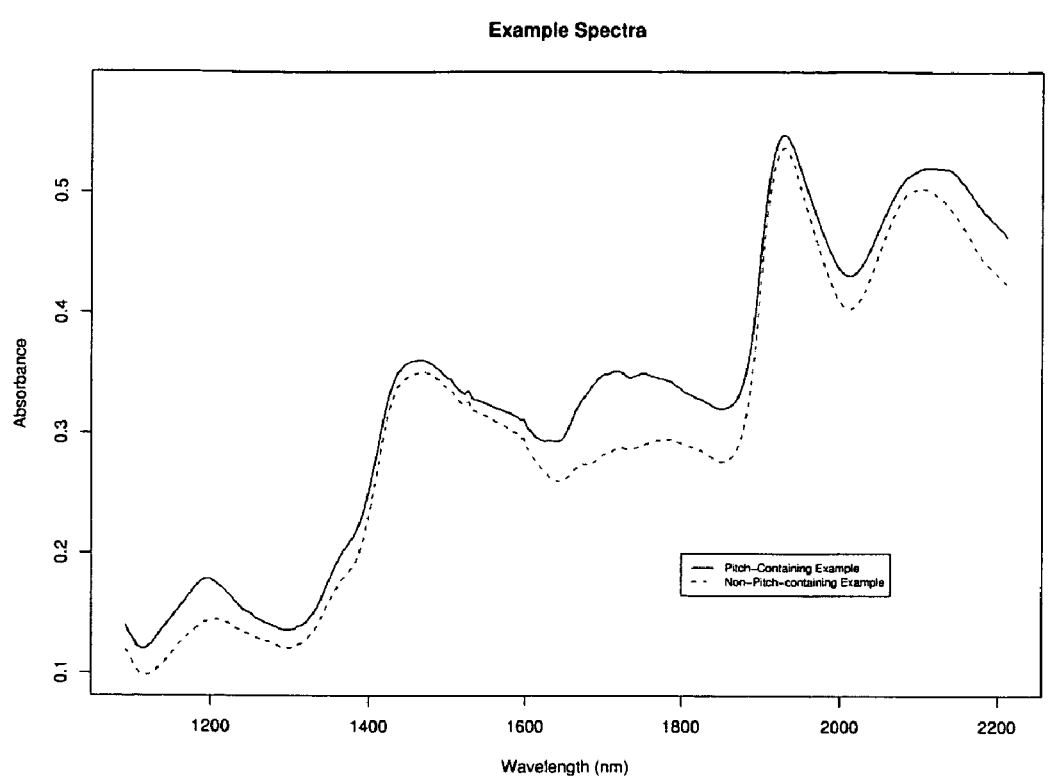
FIG. 19 is a plot of spectra for wood products based on whether the wood products contain pitch.

G. Methods of Using Multi-Sensor Data to Estimate the Shrinkage Properties of Wood by First Using the Multi-Sensor Data to Identify the Type or Class of Wood that is Being Evaluated, and then Using the Multi Sensor Data to Estimate Shrinkage Using a Class-Specific Equation and/or Algorithm Parameters calculated from multiple sensors, such as tracheid-effect line images and spectroscopy data, have shown to be useful in predicting the shrinkage properties of wood. Many of the parameters found to be associated with shrinkage are also influenced by chemical or physical features of the wood that may or may not be associated with shrinkage. For example, wood that contains pitch may be more prone to moisture-induced dimensional instability than typical clear-wood. However, both tracheid-effect images and certain spectral bands are greatly influenced by pitch in ways very different from non-pitch-containing wood with similar shrinkage properties. FIG. 19 shows two spectra. The "top" spectra is from a sample containing pitch, the other from a sample that does not contain pitch. Both wood samples have similar shrinkage behavior; however there are several important differences between these spectra, including a sharper peak at 1200 nm and a steeper rise between 1650 and 1700 nm in the pitch-containing spectrum. These spectra are typical of other pitch and non-pitch containing southern-pine samples.

This suggests that improved shrinkage estimates could be obtained by having different models or algorithms for different types of wood. Such a strategy can be accomplished with a two-step approach to shrinkage prediction. First, the wood-type of a region of interest is identified using inputs from one or more sensors (Classification Step). The type of qualitative assessment may be done with respect to a dimensional stability property, or other property. For example, the dimensional stability property which enables classification may be crook. In another embodiment, the property allowing classification may be "pith containing". Second, a class-specific shrinkage prediction model or algorithm is applied based on the results of the first step (this second step can be referred to as a Prediction Step). Examples of wood types include, but are not limited to, knots, compression-wood, pitch, pith-containing, early-wood, late-wood, species and blue-stain. The models or algorithms to classify regions of interest or to predict shrinkage behavior will typically be learned from a training set of data. Methods for classification and prediction have previously been discussed.

The classification-step will predict membership into any of K+2 categories, where K is the number of named classes (e.g., knots). The other two categories are for "outliers", namely, cases which do not look like others that have been observed, and "doubt", namely, cases in which class membership is too uncertain to make a decision. Example 10 describes a two-step approach to estimating shrinkage properties using multi-sensor data.

EXAMPLE 10

In this example, the data used were Tracheid-effect line images and NIR absorbance spectra. A training dataset consisting of approximately 350 12"×1"×¾" pieces of wood was used to build a shrinkage-coefficient calibration model. Each piece of wood was scanned for both tracheid-effect and NIR absorbance data. Several parameters were calculated from each Tracheid-effect image. In addition, each piece of wood was equilibrated at two different times in two different relative humidity environments: 20% RH and 90% RH.

Length measurements were made at each humidity level and the moisture-induced dimensional change was recorded.

Figure 20:
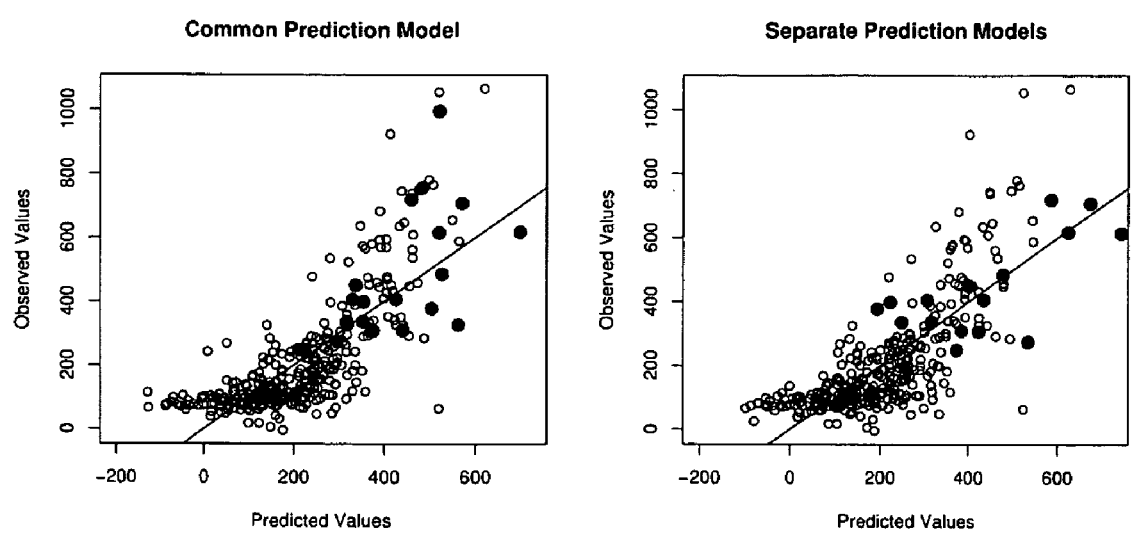
FIG. 20 is a plot of measured and predicted shrinkage values plotted against fitted values.

A partial least squares model was trained on all cases using only the NIR absorbance data. FIG. 20 illustrates two plots of results. The left-hand plot shows the measured shrinkage values plotted against the fitted values of all cases. The ratio of NIR absorbance values at 1200 nm and 1270 nm has been found to be a useful indicator for the presence of pitch. If the ratio A1200/A1270 is greater than 1.18, the sample likely contains pitch. Samples with this ratio greater than 1.18 are highlighted in the left-hand plot. The fit of these samples is rather poor. A second set of models was then developed; one only on samples with A1200/A1270 greater than 1.18, and one only on samples with this ratio less than 1.18. The right-hand plot in FIG. 20 shows the predicted results using class-specific models. That is, samples with A1200/A1270 greater than 1.18 were predicted with the model trained on the "pitch-containing" samples, while the samples with A1200/A1270 less than 1.18 were predicted with the model trained on the "non-pitch-containing" samples. The results show that the fit of the 'pitch-containing' samples is improved. The fit of the samples with the ratio less than 1.18 is also improved, although to a smaller extent than for the samples with the ratio greater than 1.18.

In other examples of the two-step prediction approach, particularly for the "outlier" or "doubt" categories, an option for the prediction-step would be to simply estimate the shrinkage value of a coupon from the average value of its neighbors. Alternatively, data from sub-regions within a coupon that have been labeled as an outlier or with doubt could be excluded from data aggregation (i.e., 'masked').

In an embodiment, a first algorithm may be provided for classifying the region of interest into a category within a plurality of categories directed to qualitative assessments of dimensional stability. A second algorithm may be provided for obtaining a quantitative estimate of dimensional stability. This second algorithm may have a set of factors, such as for example A, B, C, and D which represent different equations, respectively. A calculation performed by the second algorithm may be contingent on the classification performed via the first algorithm. For example, if via the first algorithm, the wood product is classified into a "pitch" category, factor "B" may default to zero, or some other value and/or formula. In another example, if via the first algorithm, the wood product is classified as "pith-containing", factor "D" and/or factor "C" may default to zero or other value, or be changed to another formula. Other variations based on classifications are also contemplated and may be understood by those skilled in the art.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for determining crook potential of a wood product, the method comprising the steps of:
   dividing the wood product into sections;
   dividing the sections into shrinkage coupons;
   obtaining a second derivative of a crook profile for each section of the wood product, where each second derivative is a function of the shrinkage values of the shrinkage coupons within the corresponding section: $C''=f(T1, T2, T3, \ldots, Tn)$ wherein $C''$ is the second defivative of the crook profile for each section of the wood product T values are the coupon shrinkage values for the n coupons into which the section is divided, and are determined by the product of a corresponding shrinkage rate coefficient (S) and a moisture content change (MC): $Ti=Si.times.MCi$; and
   integrating $C''$ twice to determine the crook profile of each section of the wood product.

2. The method of claim 1 wherein the section is divided into at least two shrinkage coupons across a width of the wood product.

3. The method of claim 1 wherein a single sensor group examines each section.

4. The method of claim 3 wherein the single sensor group performs a measurement selected from the group consisting of: moisture content measurement, electrical property measurement, structural property measurement, acousto-ultrasonic property measurement, light scatter (tracheid-effect) measurement, grain angle measurement, shape measurement, color measurement, spectral measurement and defect maps.

5. The method of claim 1 wherein two or more sensor groups examine each section.

6. The method of claim 5 wherein the two or more sensor groups perform at least two measurements selected from the group consisting of: moisture content measurement, electrical property measurement, structural property measurement, acousto-ultrasonic property measurement, light scatter (tracheid-effect) measurement, grain angle measurement, shape measurement, color measurement, spectral measurement and defect maps.

7. A method for determining bow potential of a wood product, the method comprising the steps of:
   dividing the wood product into sections;
   dividing the sections into shrinkage coupons;
   obtaining a second derivative of a bow profile for each section of the wood product, where each second derivative is a function of the shrinkage values of the shrinkage coupons within the corresponding section: $B''=g(T1, T2, T3, \ldots, Tn)$ where $B''$ is the second derivative of the bow profile for each section of the wood product T values are the coupon shrinkage values for the n coupons into which the section is divided, and are determined by the product of a corresponding shrinkage rate coefficient (S) and a moisture content change (MC): $Ti=Si.times.MCi$; and
   integrating $B''$ twice to determine the bow profile of each section of the wood product.

8. The method of claim 7 wherein the section is divided into at least two shrinkage coupons across a thickness of the wood product.

9. The method of claim 7 wherein a single sensor group examines each section.

10. The method of claim 9 wherein the single sensor group performs a measurement selected from the group consisting of: moisture content measurement, electrical property measurement, structural property measurement, acousto-ultrasonic property measurement, light scatter (tracheid-effect) measurement, grain angle measurement, shape measurement, color measurement, spectral measurement and defect maps.

11. The method of claim 7 wherein two or more sensor groups examine each section.

12. The method of claim 11 wherein the two or more sensor groups perform at least two measurements selected from the group consisting of: moisture content measurement, electrical property measurement, structural property measurement, acousto-ultrasonic property measurement, light scatter (tracheid-effect) measurement, grain angle measurement, shape measurement, color measurement, spectral measurement and defect maps.

* * * * *